United States Patent
Dolan et al.

(10) Patent No.: US 11,351,098 B2
(45) Date of Patent: *Jun. 7, 2022

(54) DENTIFRICE FORMULATIONS HAVING SPHERICAL STANNOUS COMPATIBLE SILICA PARTICLES FOR REDUCED RDA

(71) Applicant: The Procter & Gamble Company, Cincinnati, OH (US)

(72) Inventors: Lawrence Edward Dolan, Cincinnati, OH (US); Sanjeev Midha, Mason, OH (US); Eva Schneiderman, Mason, OH (US); Karl William Gallis, Perryville, MD (US); William Jackson Hagar, Perryville, MD (US); Terry William Nassivera, Gambrills, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/438,968

(22) Filed: Jun. 12, 2019

(65) Prior Publication Data

US 2019/0374448 A1    Dec. 12, 2019

Related U.S. Application Data

(60) Provisional application No. 62/683,961, filed on Jun. 12, 2018.

(51) Int. Cl.
*A61K 8/25* (2006.01)
*A61K 8/02* (2006.01)
*A61Q 11/00* (2006.01)

(52) U.S. Cl.
CPC ............. *A61K 8/25* (2013.01); *A61K 8/0279* (2013.01); *A61Q 11/00* (2013.01)

(58) Field of Classification Search
CPC ........ A61K 8/25; A61K 8/0279; A61K 8/025; A61Q 11/00
See application file for complete search history.

(56) References Cited

U.S. PATENT DOCUMENTS

| | | | |
|---|---|---|---|
| 4,340,583 A | 7/1982 | Wason | |
| 4,420,312 A | 12/1983 | Wason | |
| 4,421,527 A | 12/1983 | Wason | |
| 6,616,916 B1 | 9/2003 | Karpe | |
| 8,551,457 B2 | 10/2013 | Deckner | |
| 8,609,068 B2 | 12/2013 | Hagar | |
| 8,945,517 B2 | 2/2015 | Hagar | |
| 10,328,002 B2 * | 6/2019 | Dolan | ............... A61K 8/19 |
| 2011/0206746 A1 | 8/2011 | Hagar | |
| 2017/0105913 A1 | 4/2017 | Sinclair | |

FOREIGN PATENT DOCUMENTS

| | | |
|---|---|---|
| AU | 2013205147 B2 | 3/2016 |
| WO | 9634592 A1 | 11/1996 |
| WO | 2018114280 A1 | 6/2018 |
| WO | 2018118382 A1 | 6/2018 |

OTHER PUBLICATIONS

A Laboratory Method for Assessment of Dentifrice Abrasivity, Hefferren, Journal of Dental Res., Jul.-Aug. 1976, 55 (4), pp. 563-573.
Adsorption of Gases in Multimolecular Layers, Brunauer et al., J. Am. Chem. Soc., 60, 309 (1938).
Improved Ball Crater Micro-Abrasion Test Based on a Ball on Three Disk Configuration, J. M. Fildes et al., Wear 274-275 (2012) 414-422.
In Vitro Removal of Stain With Dentifrices, G. K. Stookey, et al., J. Dental Res., 61, 1236-9, 1982.
International Search Report and Written Opinion; Application No. US2019/036675; dated Oct. 1, 2019; 19 pages.

* cited by examiner

*Primary Examiner* — Lezah Roberts
(74) *Attorney, Agent, or Firm* — Parker McCrary

(57) ABSTRACT

Dentifrice containing silica particles having a d50 median particle size from 4 to 25 µm, a BET surface area of less than 10 m²/g, and a total mercury intrusion pore volume from 0.2 to 1.5 cc/g, are disclosed.

36 Claims, 8 Drawing Sheets

DENTIFRICE FORMULATIONS HAVING SPHERICAL STANNOUS COMPATIBLE SILICA PARTICLES FOR REDUCED RDA

BACKGROUND OF THE INVENTION

Compositions containing stannous, including stannous fluoride, are used in toothpaste and other dentifrice applications, providing improved cavity protection and reduced plaque, gingivitis, and tooth sensitivity. However, the effectiveness of stannous in a dentifrice composition can be diminished due to interactions with other components of the formulation, such as silica materials. Therefore, it would be beneficial to provide silica materials with improved stannous compatibility to improve the overall effectiveness of the stannous in a dentifrice composition.

Relative dentin abrasion (RDA) is a test that is used to set safety limits for toothpaste and other dentifrice compositions. The RDA test involves measuring the loss of dentin after brushing with a test toothpaste formulation relative to the control calcium pyrophosphate (set to 100). Spherical silica particles, as compared to traditional non-spherical and irregularly shaped silica particles, have certain properties (such as low Einlehner abrasion) that are beneficial for their use in toothpaste and other dentifrice applications. However, it would be advantageous for these spherical silica materials also to have improved RDA performance.

Therefore, the present invention is principally directed to a dentifrice comprising spherical silica particles having a beneficial combination of both improved stannous compatibility and improved RDA performance.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Dentifrice having silica particles with reduced Relative Dentin Abrasion (RDA) and increased stannous compatibility are disclosed and described herein.

A dentifrice composition is provided that comprises binder; surfactant; silica particles; wherein the silica particles comprise a d50 median particle size in a range from about 4 to about 25 µm; a BET surface area in a range from 0 to about 10 m²/g; and a total mercury intrusion pore volume in a range from about 0.2 to about 1.5 cc/g.

In accordance with an aspect of this invention, such silica particles can have (i) a d50 median particle size in a range from about 4 to about 25 µm (or from about 6 to about 25 µm, or from about 8 to about 20 µm), (ii) a sphericity factor ($S_{80}$) of greater than or equal to about 0.9 (or greater than or equal to about 0.92), (iii) a BET surface area in a range from 0 to about 10 m²/g (or from about 0.05 to about 8 m²/g), and (iv) a total mercury intrusion pore volume in a range from about 0.35 to about 1.1 cc/g (or from about 0.35 to about 0.7 cc/g, or from about 0.4 to about 0.65 cc/g). These silica particles have a spherical shape or morphology, and can be produced using a continuous loop reactor process.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DETAILED DESCRIPTION OF THE INVENTION

Figure 1:
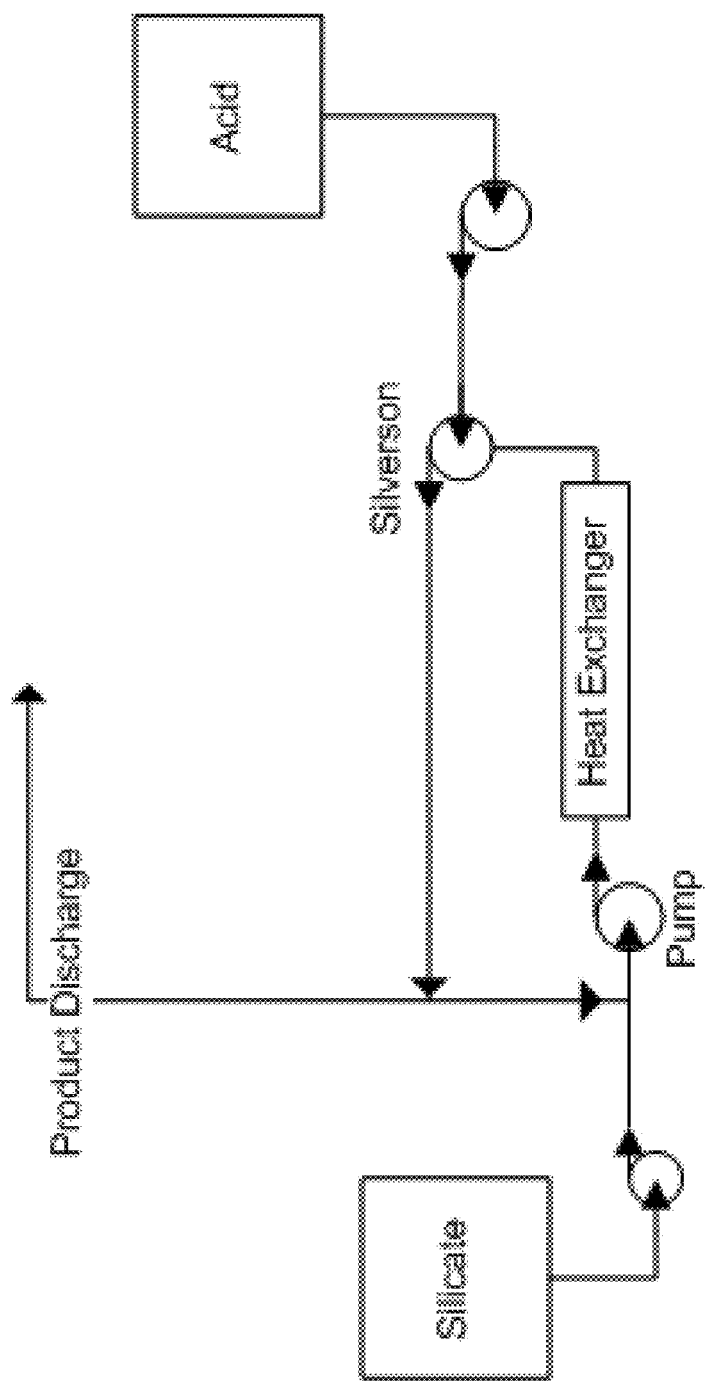
FIG. 1 is a schematic of the continuous loop reactor apparatus used to produce the silica products of Examples 2A-6A.
Figure 2:
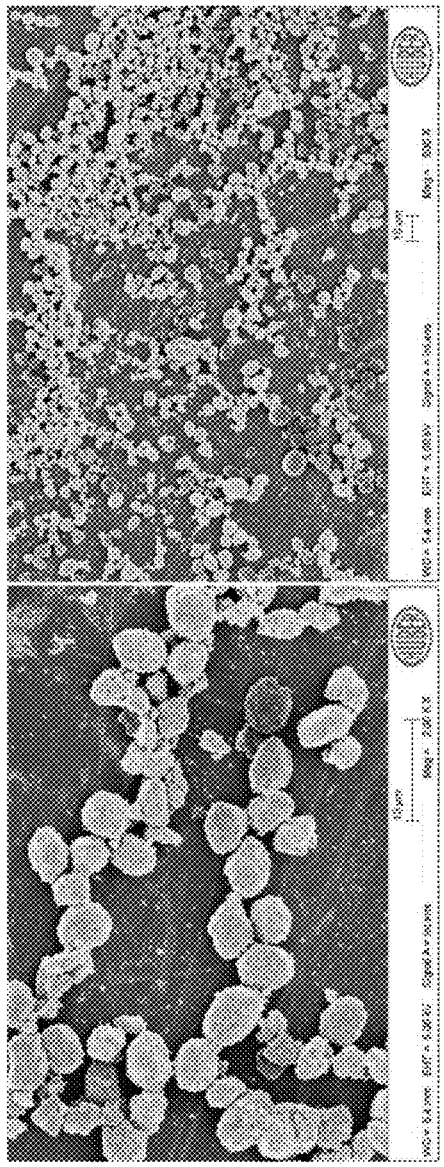
FIG. 2 is Scanning Electron Micrographs of the silica of Example 2A.
Figure 3:
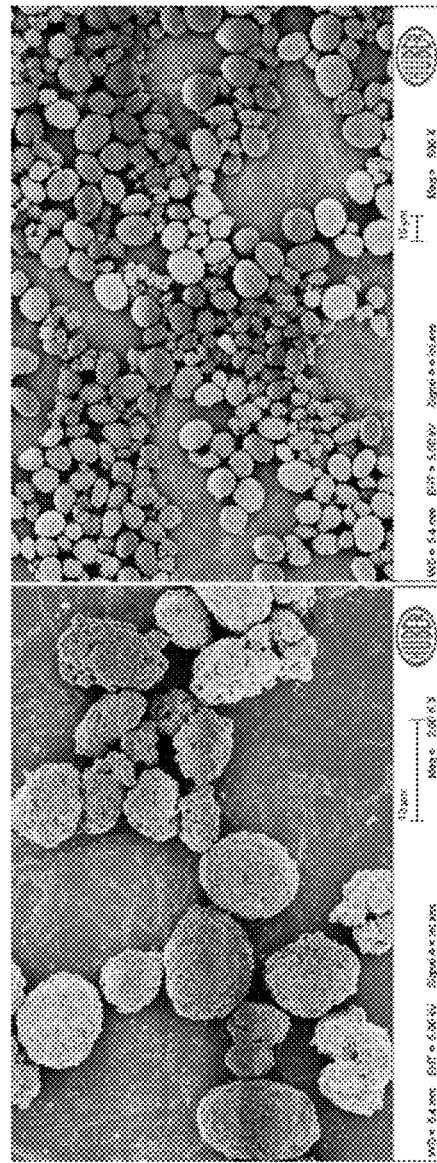
FIG. 3 is Scanning Electron Micrographs of the silica of Example 3A.
Figure 4:
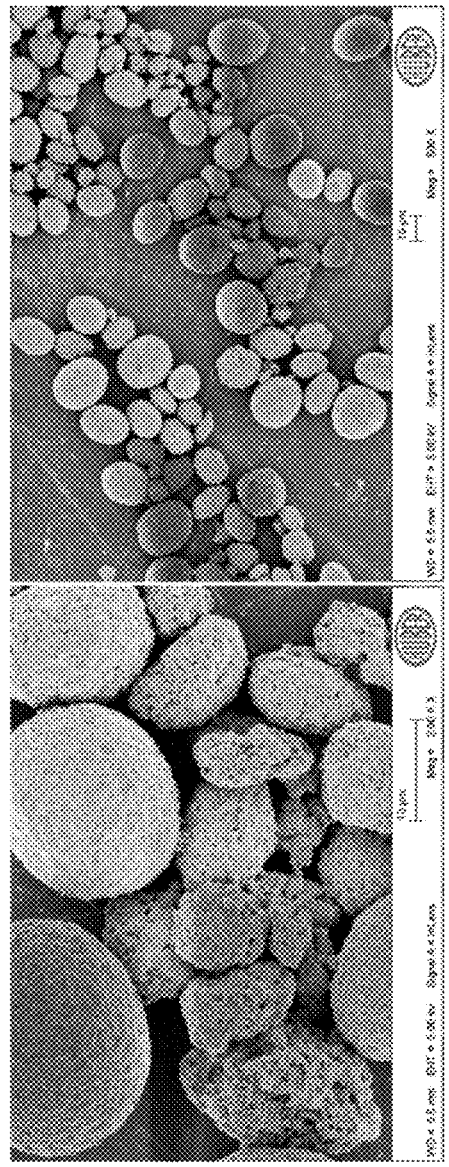
FIG. 4 is Scanning Electron Micrographs of the silica of Example 4A.
Figure 5:
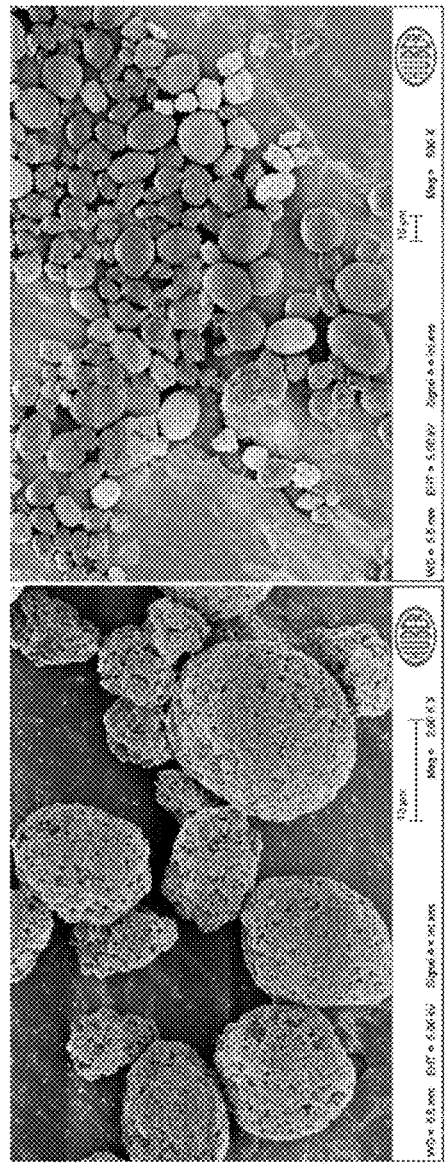
FIG. 5 is Scanning Electron Micrographs of the silica of Example 5A.

Disclosed herein are dentifrices having generally spherical silica particles that can be characterized by (i) a d50 median particle size in a range from about 4 to about 25 µm (or from about 6 to about 25 µm, or from about 8 to about 20 µm), (ii) a sphericity factor ($S_{80}$) of greater than or equal to about 0.9 (or greater than or equal to about 0.92), (iii) a BET surface area in a range from 0 to about 10 m²/g (or from about 0.05 to about 8 m²/g), and (iv) a total mercury intrusion pore volume in a range from about 0.35 to about 1.1 cc/g (or from about 0.35 to about 0.7 cc/g, or from about 0.4 to about 0.65 cc/g). Methods of making these spherical silica particles, and dentifrice compositions containing the spherical particles, also are disclosed and described herein.

Beneficially, the spherical particles disclosed and described herein have an unexpected combination of low RDA and high stannous compatibility.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated and can be interchanged, with or without explicit description of the particular combination. Accordingly, unless explicitly recited otherwise, any aspect or feature disclosed herein can be combined to describe inventive designs, compositions, processes, or methods consistent with the present disclosure.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival—paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "teeth", as used herein, refers to natural teeth as well as artificial teeth or dental prosthesis and is construed to comprise one tooth or multiple teeth. The term "tooth surface" as used herein, refers to natural tooth surface(s) as well as artificial tooth surface(s) or dental prosthesis surface(s) accordingly.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example X or Y, means X or Y or both.

As used herein, the articles "a" and "an" are understood to mean one or more of the material that is claimed or described, for example, "an oral care composition" or "a bleaching agent."

All measurements referred to herein are made at about 23° C. (i.e. room temperature) unless otherwise specified.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, and so forth.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. As a representative example, the BET surface area of the silica particles can be in certain ranges in various aspects of this invention. By a disclosure that the BET surface area is in a range from 0 to about 10 $m^2/g$, the intent is to recite that the surface area can be any surface area within the range and, for example, can be equal to about 0.1, about 0.5, about 1, about 2, about 3, about 4, about 5, about 6, about 7, about 8, about 9, or about 10 $m^2/g$. Additionally, the surface area can be within any range from 0 to about 10 $m^2/g$ (for example, from about 0.05 to about 8 $m^2/g$), and this also includes any combination of ranges between 0 and about 10 $m^2/g$ (for example, the surface area can be in a range from about 0.1 to about 3, or from about 5 to about 7 $m^2/g$). Likewise, all other ranges disclosed herein should be interpreted in a manner similar to this example.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

Spherical Silica Particles

An illustrative and non-limiting example of silica particles consistent with the present invention can have the following characteristics: (i) a d50 median particle size in a range from about 4 to about 25 µm, (ii) a sphericity factor ($S_{80}$) of greater than or equal to about 0.9, (iii) a BET surface area in a range from 0 to about 10 $m^2/g$, and (iv) a total mercury intrusion pore volume in a range from about 0.2 to about 1.5 cc/g. Another illustrative and non-limiting example of silica particles consistent with the present invention can have the following characteristics: (i) a d50 median particle size in a range from about 6 to about 25 µm, (ii) a sphericity factor ($S_{80}$) of greater than or equal to about 0.9, (iii) a BET surface area in a range from 0 to about 8 $m^2/g$, and (iv) a total mercury intrusion pore volume in a range from about 0.35 to about 1.1 cc/g. Yet another illustrative and non-limiting example of silica particles consistent with the present invention can have the following characteristics: (i) a d50 median particle size in a range from about 8 to about 20 µm, (ii) a sphericity factor ($S_{80}$) of greater than or equal to about 0.9, (iii) a BET surface area in a range from 0 to about 8 m²/g, and (iv) a total mercury intrusion pore volume in a range from about 0.35 to about 0.7 cc/g. In further aspects, such silica particles consistent with the present invention also can have any of the characteristics or properties provided below, and in any combination.

In an aspect, the spherical silica particles can have a relatively large average particle size. Often, the median particle size (d50) and/or mean particle size (average) can fall within a range from about 4 to about 25, from about 4 to about 20, from about 6 to about 25, from about 6 to about 22, from about 6 to about 18, from about 7 to about 25, from about 7 to about 20, or from about 7 to about 18 μm, and the like. In another aspect, the median particle size (d50) and/or mean particle size (average) can fall within a range from about 8 to about 25, from about 8 to about 20, from about 8 to about 18, from about 8 to about 15, from about 9 to about 16, or from about 9 to about 14 μm. Other appropriate ranges for the mean and median particle sizes are readily apparent from this disclosure.

The spherical particles also have a very narrow particle size distribution, which can be quantified by the ratio of (d90-d10)/d50. A lower value for the ratio indicates a narrower particle size distribution, while a larger value for the ratio indicates a broader particle size distribution. Generally, the spherical particles disclosed herein can be characterized by a ratio of (d90-d10)/d50 in a range from about 1.1 to about 2.4. In one aspect, the ratio of (d90-d10)/d50 can be in a range from about 1.1 to about 2.2, while in another aspect, the ratio of (d90-d10)/d50 can be in a range from about 1.1 to about 2, from about 1.1 to about 1.7, or from about 1.3 to about 1.5. Yet, in another aspect, the ratio of (d90-d10)/d50 can be in a range from about 1.2 to about 2.4, while in still another aspect, the ratio of (d90-d10)/d50 can be in a range from about 1.2 to about 2.2, or from about 1.2 to about 2. Other appropriate ranges for the ratio of (d90-d10)/d50 are readily apparent from this disclosure.

Another indicator of the narrow particle size distribution of the spherical silica particles is the weight percentage of 325 mesh residue (amount retained in a 325 mesh sieve), which can be less than or equal to about 1.2 wt. %. In some aspects, the 325 mesh residue can be less than or equal to about 1 wt. %, less than or equal to about 0.75 wt. %, less than or equal to about 0.6 wt. %, or less than or equal to about 0.3 wt. %. Other appropriate ranges for the 325 mesh residue are readily apparent from this disclosure.

Sphericity of the spherical silica particles can be quantified by a sphericity factor ($S_{80}$), which can be greater than or equal to about 0.85, greater than or equal to about 0.88, or greater than or equal to about 0.9. The sphericity factor ($S_{80}$) is determined as follows. An SEM image of the silica particle sample is magnified 20,000 times, which is representative of the silica particle sample, and is imported into photo imaging software, and the outline of each particle (two-dimensionally) is traced. Particles that are close in proximity to one another but not attached to one another should be considered separate particles for this analysis. The outlined particles are then filled in with color, and the image is imported into particle characterization software (e.g., IMAGE-PRO PLUS available from Media Cybernetics, Inc., Bethesda, Md.) capable of determining the perimeter and area of the particles. Sphericity of the particles can then be calculated according to the equation, Sphericity=(perimeter)² divided by (4π×area), wherein perimeter is the software measured perimeter derived from the outlined trace of the particles, and wherein area is the software measured area within the traced perimeter of the particles.

The sphericity calculation is performed for each particle that fits entirely within the SEM image. These values are then sorted by value, and the lowest 20% of these values are discarded. The remaining 80% of these values are averaged to obtain the sphericity factor ($S_{80}$). Additional information on sphericity can be found in U.S. Pat. Nos. 8,945,517 and 8,609,068, incorporated herein by reference in their entirety.

In one aspect of this invention, the spherical silica particles can have a sphericity factor ($S_{80}$) greater than or equal to about 0.85, or greater than or equal to about 0.88, while in another aspect, the sphericity factor ($S_{80}$) can be greater than or equal to about 0.9. Yet, in another aspect, the spherical silica particles can be characterized by a sphericity factor ($S_{80}$) greater than or equal to about 0.92, and in still another aspect, the silica particles can be characterized by a sphericity factor ($S_{80}$) greater than or equal to about 0.94. As one of skill in the art would readily recognize, a 3-dimensional sphere (or 2-dimensional circle) will have a sphericity factor ($S_{80}$) equal to 1.

In an aspect, the silica particles can have a very low surface area, generally a BET surface area ranging from 0 to about 10 m²/g. Often, the BET surface area can fall within a range from about 0.05 to about 10, from about 0.1 to about 10, from about 0.25 to about 10, or from about 0.05 to about 8 m²/g. In further aspects, the BET surface area can be in a range from about 0.25 to about 8, from about 0.5 to about 8, from about 0.1 to about 5, from about 0.25 to about 5, from about 0.5 to about 5, from about 0.25 to about 3.5, or from about 0.5 to about 2 m²/g, and the like. The BET surface area also can fall within a range from 0 to about 8 m²/g, from 0 to about 5 m²/g, or from 0 to about 3 m²/g. Other appropriate ranges for the BET surface area are readily apparent from this disclosure.

Likewise, the total mercury intrusion pore volume of the silica particles is also relatively low, often falling within a range from about 0.2 to about 1.5, from about 0.3 to about 1.1, from about 0.35 to about 1.1, from about 0.35 to about 0.7, from about 0.35 to about 0.65, from about 0.35 to about 0.62, or from about 0.35 to about 0.6 cc/g. In another aspect, the total mercury intrusion pore volume of the silica particles can be from about 0.4 to about 0.7 cc/g, from about 0.4 to about 0.65 cc/g, from about 0.45 to about 0.65 cc/g, or from about 0.49 to about 0.6 cc/g. Other appropriate ranges for the total mercury intrusion pore volume are readily apparent from this disclosure.

Additionally, the spherical silica particles can be less abrasive, as reflected by an Einlehner abrasion value ranging from about 7 to about 25 mg lost/100,000 revolutions. For instance, the Einlehner abrasion value can be in a range from about 8 to about 20; alternatively, from about 10 to about 20; or alternatively, from about 15 to about 22 mg lost/100,000 revolutions. The Einlehner abrasion value also can be in a range from about 10 to about 25 mg lost/100,000 revolutions, from about 10 to about 22 mg lost/100,000 revolutions, or from about 11 to about 17 mg lost/100,000 revolutions. Other appropriate ranges for the Einlehner abrasion value are readily apparent from this disclosure.

Likewise, these spherical silica particles also have a relatively high pour density. In one aspect, the pour density can be in a range from about 30 to about 65 lb/ft³, or from about 40 to about 65 lb/ft³. In another aspect, the pour density can be in a range from about 40 to about 62 lb/ft³, from about 42 to about 60 lb/ft³, or from about 43 to about 58 lb/ft³. In yet another aspect, the pour density can be in the range from about 42 to about 56 lb/ft³, or from about 44 to about 54 lb/ft³. Other appropriate ranges for the pour density are readily apparent from this disclosure.

Spherical silica particles in accordance with aspects of this invention can have excellent stannous compatibility and excellent CPC compatibility. Typically, the spherical silica particles described herein have a stannous compatibility from about 40 to about 99%, such as, for instance, from about 80 to about 99%, from about 75 to about 98%, from about 75 to about 95%, from about 80 to about 95%, from about 82 to about 98%, or from about 86 to about 93%, and the like. Additionally, the spherical silica particles typically have a CPC compatibility from about 55 to about 99%, such as, for instance, from about 40 to about 95%, from about 75 to about 95%, from about 78 to about 95%, or from about 81 to about 91%, and the like. Other appropriate ranges for the stannous compatibility and CPC compatibility are readily apparent from this disclosure.

In another aspect, the spherical silica particles can have relatively low oil absorption, relatively low water absorption, and very low CTAB surface area. For instance, the oil absorption can be in a range from about 20 to about 75 cc/100 g, from about 25 to about 60 cc/100 g, from about 25 to about 55 cc/100 g, or from about 32 to about 50 cc/100 g. Additionally or alternatively, the water absorption can be in a range from about 40 to about 75 cc/100 g, from about 45 to about 72 cc/100 g, from about 50 to about 70 cc/100 g, from about 50 to about 65 cc/100 g, or from about 57 to about 66 cc/100 g. Representative and non-limiting ranges for the CTAB surface include from 0 to about 10 $m^2/g$, from 0 to about 6 $m^2/g$, from 0 to about 4 $m^2/g$, or from 0 to about 2 $m^2/g$. Other appropriate ranges for the oil absorption, the water absorption, and the CTAB surface area are readily apparent from this disclosure.

While not limited thereto, the disclosed spherical silica particles can have a loss on drying (LOD) that often falls within a range from about 1 to about 10 wt. %. Illustrative and non-limiting ranges for the LOD include from about 1 to about 8 wt. %, from about 2 to about 8 wt. %, from about 1 to about 7 wt. %, from about 1 to about 5 wt. %, from about 1 to about 4 wt. %, or from about 1.5 to about 2 wt. %. Likewise, while not limited thereto, the disclosed spherical silica particles can have a loss on ignition (LOI) that often falls within a range from about 3 to about 10 wt. %. Illustrative and non-limiting ranges for the LOI include from about 3 to about 8 wt. %, from about 3 to about 7 wt. %, from about 3 to about 6 wt. %, from about 3.5 to about 9 wt. %, from about 3.5 to about 7.5 wt. %, or from about 3.5 to about 6 wt. %. Other appropriate ranges for the LOD and LOI are readily apparent from this disclosure.

Generally, the spherical silica particles can have a substantially neutral pH that encompasses, for instance, a pH range of from about 5.5 to about 9, from about 6.2 to about 8.5, or from about 6.8 to about 8.2. Other appropriate ranges for the pH are readily apparent from this disclosure.

The Relative Dentin Abrasion (RDA) test is typically performed to confirm that a dentifrice composition, e.g., toothpaste, is safe for consumer use, with the upper limit of the test set at 250. Unexpectedly, the results provided herein demonstrate that, for the spherical silica particles consistent with this invention, the RDA generally decreases as the median particle size (d50) and/or mean particle size (average) increases. The spherical silica particles can be characterized by a RDA at 20 wt. % loading of less than about 250, or in a range from about 100 to about 220, in one aspect of this invention, and from about 120 to about 200 in another aspect. Other illustrative and non-limiting ranges for the RDA at 20 wt. % loading can include from about 50 to about 200, from about 80 to about 200, from about 80 to about 150, from about 130 to about 190, from about 130 to about 180, from about 150 to about 200, from about 150 to about 190, or from about 168 to about 182. Other appropriate ranges for the RDA are readily apparent from this disclosure.

The spherical silica particles also can be described by their Pellicle Cleaning Ratio (PCR), which is a measure of the cleaning characteristics of a dentifrice composition containing the silica particles. The silica particles can be characterized by a PCR at 20 wt. % loading in a range about 70 to about 130, from about 80 to about 130, from about 70 to about 120, from about 80 to about 120, or from about 90 to about 110. The PCR/RDA ratio (at 20 wt. % loading) often can be from about 0.4:1 to about 1.1:1, from about 0.4:1 to about 0.8:1, from about 0.5:1 to about 1:1, from about 0.5:1 to about 0.7:1, from about 0.45:1 to about 0.65:1, or from about 0.56:1 to about 0.57:1.

In these and other aspects, any of the spherical silica particles can be amorphous, can be synthetic, or can be both amorphous and synthetic. Moreover, the spherical silica particles can comprise (or consist essentially of, or consist of) precipitated silica particles in particular aspects of this invention, although not limited thereto.

Dentifrice Compositions

The spherical silica particles can be used in any suitable composition and for any suitable end-use application. Often, the silica particles can be used in oral care applications, such as in a dentifrice composition. The dentifrice composition can contain any suitable amount of the silica particles, such as from about 0.5 to about 50 wt. %, from about 1 to about 50 wt. %, from about 5 to about 35 wt. %, from about 10 to about 40 wt. %, or from about 10 to about 30 wt. %, of the spherical silica particles. These weight percentages are based on the total weight of the dentifrice composition.

The dentifrice composition can be in any suitable form, such as a solid, liquid, powder, paste, or combinations thereof. In addition to the silica particles, the dentifrice composition can contain other ingredients or additives, non-limiting examples of which can include a humectant, a solvent, a binder, a therapeutic agent, a chelating agent, a thickener other than the silica particles, a surfactant, an abrasive other than the silica particles, a sweetening agent, a colorant, a flavoring agent, a preservative, and the like, as well as any combination thereof.

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, and mixtures thereof. In some formulations, humectants are present in an amount from about 20 to about 50 wt. %, based on the weight of the dentifrice composition.

A solvent can be present in the dentifrice composition, at any suitable loading, and usually the solvent comprises water. When used, water is preferably deionized and free of impurities, can be present in the dentifrice at loadings from 5 to about 70 wt. %, or from about 5 to about 35 wt. %, based on the weight of dentifrice composition.

Therapeutic agents also can be used in the compositions of this invention to provide for the prevention and treatment of dental caries, periodontal disease, and temperature sensitivity, for example. Suitable therapeutic agents can include, but are not limited to, fluoride sources, such as sodium fluoride, sodium monofluorophosphate, potassium monofluorophosphate, stannous fluoride, potassium fluoride, sodium fluorosilicate, ammonium fluorosilicate and the like; condensed phosphates such as tetrasodium pyrophosphate, tetrapotassium pyrophosphate, disodium dihydrogen pyrophosphate, trisodium monohydrogen pyrophosphate; tripolyphosphates, hexametaphosphates, trimetaphosphates and pyrophosphates; antimicrobial agents such as triclosan, bisguanides, such as alexidine, chlorhexidine and chlorhexidine gluconate; enzymes such as papain, bromelain, glucoamylase, amylase, dextranase, mutanase, lipases, pectinase, tannase, and proteases; quaternary ammonium compounds, such as benzalkonium chloride (BZK), benzethonium chloride (BZT), cetylpyridinium chloride (CPC), and domiphen bromide; metal salts, such as zinc citrate, zinc chloride, and stannous fluoride; sanguinaria extract and sanguinarine; volatile oils, such as eucalyptol, menthol, thymol, and methyl salicylate; amine fluorides; peroxides and the like. Therapeutic agents can be used in dentifrice formulations singly or in combination, and at any therapeutically safe and effective level or dosage.

Thickening agents are useful in the dentifrice compositions to provide a gelatinous structure that stabilizes the toothpaste against phase separation. Suitable thickening agents include silica thickener; starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof. Typical levels of thickening agents or binders are up to about 15 wt. % of a toothpaste or dentifrice composition.

Useful silica thickeners for utilization within a toothpaste composition, for example, include, as a non-limiting example, an amorphous precipitated silica such as ZEODENT® 165 silica. Other non-limiting silica thickeners include ZEODENT® 153, 163, and 167, and ZEOFREE® 177 and 265 silica products, all available from Evonik Corporation, and AEROSIL® fumed silicas.

Surfactants can be used in the dentifrice compositions of the invention to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants, such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like. Sodium lauryl sulfate is a preferred surfactant. The surfactant is typically present in the compositions of the present invention in an amount from about 0.1 to about 15 wt. %, from about 0.3 to about 5 wt. %, or from about 0.3 to about 2.5 wt. %.

The disclosed silica particles can be utilized alone as the abrasive in the dentifrice composition, or as an additive or co-abrasive with other abrasive materials discussed herein or known in the art. Thus, any number of other conventional types of abrasive additives can be present within the dentifrice compositions of the invention. Other such abrasive particles include, for example, precipitated calcium carbonate (PCC), ground calcium carbonate (GCC), chalk, bentonite, dicalcium phosphate or its dihydrate forms, silica gel (by itself, and of any structure), precipitated silica, amorphous precipitated silica (by itself, and of any structure as well), perlite, titanium dioxide, dicalcium phosphate, calcium pyrophosphate, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the dentifrice compositions to tailor the polishing characteristics of the target formulation.

Sweeteners can be added to the dentifrice composition (e.g., toothpaste) to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Flavoring agents also can be added to dentifrice compositions. Suitable flavoring agents include, but are not limited to, oil of wintergreen, oil of peppermint, oil of spearmint, oil of sassafras, and oil of clove, cinnamon, anethole, menthol, thymol, eugenol, eucalyptol, lemon, orange and other such flavor compounds to add fruit notes, spice notes, etc. These flavoring agents generally comprise mixtures of aldehydes, ketones, esters, phenols, acids, and aliphatic, aromatic and other alcohols.

Preservatives also can be added to the compositions of the present invention to prevent bacterial growth. Suitable preservatives approved for use in oral compositions such as methylparaben, propylparaben and sodium benzoate can be added in safe and effective amounts.

Other ingredients can be used in the dentifrice composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

The multipoint BET surface areas disclosed herein were determined on a Micromeritics TriStar II 3020 V1.03, using the BET nitrogen adsorption method of Brunaur et al., J. Am. Chem. Soc., 60, 309 (1938).

Mercury total intruded volumes were measured on a Micromeritics AutoPore IV 9520, previously calibrated with a silica-alumina reference material available from Micromeritics. As generally known (see Halsey, G. D., J. Chem. Phys. (1948), 16, 931), the mercury porosimetry technique is based on the intrusion of mercury into a porous structure under stringently controlled pressures. From the pressure versus intrusion data, the instrument generates volume and size distributions using the Washburn equation. Since mercury does not wet most substances and will not spontaneously penetrate pores by capillary action, it must be forced into the pores by the application of external pressure. The required pressure is inversely proportional to the size of the pores, and only slight pressure is required to intrude mercury into large macropores, whereas much greater pressures are required to force mercury into micropores. Higher pressures are required to measure the pore sizes and surface areas of the micropores present on the surfaces of silica products disclosed herein.

The total intruded volume (HgI) was measured by mercury porosimetry using a Micromeritics Autopore IV 9520. Samples were dried at 105° C. for two hours prior to analysis. The pore diameters were calculated by the Washburn equation employing a contact angle Theta ($\theta$) equal to 130° and a surface tension gamma equal to 484 dynes/cm. Mercury was forced into the voids of the material (both internal and intraparticle porosity) as a function of pressure, and the volume of the mercury intruded per gram of sample was calculated at each pressure setting. Total mercury intrusion pore volume expressed herein represents the cumulative volume of mercury intruded at pressures from vacuum to 60,000 psi. Increments in volume ($cm^3/g$) at each pressure setting were plotted against the pore radius or diameter corresponding to the pressure setting increments. The peak in the intruded volume versus pore radius or diameter curve corresponds to the mode in the pore size distribution and identifies the most common pore size in the sample. Specifically, sample size was adjusted to achieve a stem volume of 30-50% in a powder penetrometer with a 5 mL bulb and a stem volume of about 1.1 mL. Samples were evacuated to a pressure of 50 μm of Hg and held for 5 minutes. Mercury filled the pores from 4 to 60,000 psi with a 10 second equilibrium time at each of approximately 150 data collection points.

CTAB surface areas disclosed herein were determined by absorption of CTAB (cetyltrimethylammonium bromide) on the silica surface, the excess separated by centrifugation and the quantity determined by titration with sodium lauryl sulfate using a surfactant electrode. Specifically, about 0.5 grams of the silica particles were placed in a 250-mL beaker with 100 mL CTAB solution (5.5 g/L), mixed on an electric stir plate for 1 hour, then centrifuged for 30 min at 10,000 RPM. One mL of 10% Triton X-100 was added to 5 mL of the clear supernatant in a 100-mL beaker. The pH was adjusted to 3-3.5 with 0.1 N HCl and the specimen was titrated with 0.01 M sodium lauryl sulfate using a surfactant electrode (Brinkmann SUR1501-DL) to determine the endpoint.

The median particle size (d50) refers to the particle size for which 50% of the sample has a smaller size and 50% of the sample has a larger size. Median particle size (d50), mean particle size (average), d90, and d10 were determined via the laser diffraction method using a Horiba LA 300 instrument. Samples were de-agglomerated using ultrasonic vibration for 2 minutes.

For pour density and pack density, 20 grams of the sample were placed into a 250 mL graduated cylinder with a flat rubber bottom. The initial volume was recorded and used to calculate the pour density by dividing it into the weight of sample used. The cylinder was then placed onto a tap density machine where it was rotated on a cam at 60 RPM. The cam is designed to raise and drop the cylinder a distance of 5.715 cm once per second, until the sample volume is constant, typically for 15 min. This final volume was recorded and used to calculate the pack density by dividing it into the weight of sample used.

The Einlehner abrasion value is a measure of the hardness/abrasiveness of silica particles, and is described in detail in U.S. Pat. No. 6,616,916, incorporated herein by reference, and involves an Einlehner AT-1000 Abrader generally used as follows: (1) a Fourdrinier brass wire screen is weighed and exposed to the action of a 10% aqueous silica suspension for a fixed length of time; (2) the amount of abrasion is then determined as milligrams of brass lost from the Fourdrinier wire screen per 100,000 revolutions (mg lost/100,000 revolutions).

CPC compatibility (%) was determined as follows. 27 grams of a 0.3% solution of CPC (cetylpyridinium chloride) were added to a 3 g sample of the silica to be tested. The silica was previously dried at 105° C. to 150° C. to a moisture content of 2% or less, and the pH of the sample was measured to ensure the 5% pH was between 5.5 and 7.5. The mixture was shaken for a period of 10 minutes. Accelerated aging testing requires agitation of the test specimen for 1 week at 140° C. After agitation was complete, the sample was centrifuged and 5 mL of the supernatant was passed through a 0.45 μm PTFE milli-pore filter and discarded. An additional 2 g of supernatant was then passed through the same 0.45 μm PTFE milli-pore filter and then added to a vial containing 38 g of distilled water. After mixing, an aliquot of the sample was placed in a cuvette (methyl methacrylate) and the U.V. absorbance was measured at 268 nm. Water was used as a blank. The % CPC compatibility was determined by expressing as a percentage the absorbance of the sample to that of a CPC standard solution prepared by this procedure with the exception that no silica was added.

Stannous compatibility (%) was determined as follows. A stock solution containing 431.11 g of 70% sorbitol, 63.62 g of de-oxygenated deionized water, 2.27 g of stannous chloride dihydrate, and 3 g of sodium gluconcate was prepared. 34 g of the stock solution was added to a 50 mL centrifuge tube containing 6 g of the silica sample to be tested. The centrifuge tube was placed on a rotating wheel at 5 RPM and was aged for 1 week at 40° C. After aging, the centrifuge tube was centrifuged at 12,000 RPM for 10 minutes, and the stannous concentration in the supernatant was determined by ICP-OES (inductively coupled plasma optical emission spectrometer). The stannous compatibility was determined by expressing the stannous concentration of the sample as a percentage of the stannous concentration of a solution prepared by the same procedure, but with no silica added.

Oil absorption values were determined in accordance with the rub-out method described in ASTM D281 using linseed oil (cc oil absorbed per 100 g of the particles). Generally, a higher oil absorption level indicates a particle with a higher level of large pore porosity, also described as higher structure.

Water absorption values were determined with an Absorptometer "C" torque rheometer from C.W. Brabender Instruments, Inc. Approximately ⅓ of a cup of the silica sample was transferred to the mixing chamber of the Absorptometer and mixed at 150 RPM. Water then was added at a rate of 6 mL/min, and the torque required to mix the powder was recorded. As water is absorbed by the powder, the torque will reach a maximum as the powder transforms from free-flowing to a paste. The total volume of water added when the maximum torque was reached was then standardized to the quantity of water that can be absorbed by 100 g of powder. Since the powder was used on an as received basis (not previously dried), the free moisture value of the powder was used to calculate a "moisture corrected water AbC value" by the following equation.

$$\text{Water Absorption} = \frac{\text{water absorbed (cc)} + \% \text{ moisture}}{(100 \text{ (g)} - \% \text{ moisture})/100}$$

The Absorptometer is commonly used to determine the oil number of carbon black in compliance with ASTM D 2414 methods B and C and ASTM D 3493.

The pH values disclosed herein (5% pH) were determined in an aqueous system containing 5 wt. % solids in deionized water using a pH meter.

The 325 mesh residue (wt. %) of the silica sample was measured utilizing a U.S. Standard Sieve No. 325, with 44 micron or 0.0017 inch openings (stainless steel wire cloth), by weighing a 10.0 gram sample to the nearest 0.1 gram into the cup of a 1 quart Hamilton mixer (Model No. 30), adding approximately 170 mL of distilled or deionized water, and stirring the slurry for at least 7 min. The mixture was transferred onto the 325 mesh screen and water was sprayed directly onto the screen at a pressure of 20 psig for two minutes, with the spray head held about four to six inches from the screen. The remaining residue was then transferred to a watch glass, dried in an oven at 150° C. for 15 min, then cooled, and weighed on an analytical balance.

Loss on drying (LOD) was performed by measuring the weight loss (wt. %) of a sample of the silica particles after drying at 105° C. for 2 hours. Loss on ignition (LOI) was performed by measuring the weight loss (wt. %) of a pre-dried sample (after drying at 105° C. for 2 hours) of the silica particles after heating at 1000° C. for 1 hour (USP NF for $SiO_2$ method).

The cleaning performance of the silica materials in a dentifrice composition is typically quantified by a Pellicle Cleaning Ratio ("PCR") value. The PCR test measures the ability of a dentifrice composition to remove pellicle film from a tooth under fixed brushing conditions. The PCR test is described in "In Vitro Removal of Stain with Dentifrice" G. K. Stookey, et al., J. Dental Res., 61, 1236-9, 1982, which is incorporated herein by reference for its teaching of PCR. PCR values are unitless.

The Relative Dentin Abrasion (RDA) values of the dentifrice compositions of the invention were determined according to the method set forth by Hefferen, Journal of Dental Res., July-August 1976, 55 (4), pp. 563-573, and described in Wason U.S. Pat. Nos. 4,340,583, 4,420,312 and 4,421,527, which are each incorporated herein by reference for their teaching of RDA measurements. RDA values are unitless.

Examples 1A-6A

Comparative Silica Particles and Spherical Silica Particles

Example 1A was a conventional silica material commercially available from Evonik Corporation, which has an irregular and non-spherical particle morphology.

For Examples 2A-6A, a continuous loop reactor process (see e.g., U.S. Pat. Nos. 8,945,517 and 8,609,068) was used to produce silica particles. FIG. 1 illustrates the continuous loop reactor apparatus, which was configured in a recycle loop such that reaction slurry was circulated numerous times before it was discharged. The loop was comprised of sections of fixed pipe joined together by sections of flexible hose. The internal diameter of the piping/hose was approximately 1". On one side of the loop, a pump was placed to circulate the reaction slurry, and on the opposite side a Silverson in-line mixer was installed to provide additional shear to the system and also to feed the acid component. In between the pumps, a static mixer heat exchanger was installed to provide a means to control the temperature during production of the silica material. The discharge pipe, located after the acid addition point, allowed the product to discharge as a function of the rates at which silicate and acid were added. The discharge pipe also was fitted with a back pressure valve to enable the system to operate at temperatures greater than 100° C. The product discharge pipe was oriented to collect product into a tank for additional modification (e.g., pH adjustment), or was discharged directly into a rotary or press type filter. Optionally, acid could be added into the product discharge line to avoid pH adjustment when the silica product was prepared at a pH greater than 7.0.

For certain examples, the Silversion in-line mixer was modified to provide a high level of mixing without providing shear. This was accomplished by removing the stator screen from the Silverson mixer and operating the unit with only the backing plate and the normal mixer head. Particle size thus could be controlled by changing the Silverson output rate and the recirculation rate (e.g., a reduction in both rates can increase the average particle size).

Prior to the introduction of acid and silicate into the system for Examples 2A-6A, precipitated silica, sodium sulfate, sodium silicate and water were added and recirculated at 80 L/min. This step was performed to fill the recycle loop with the approximate contents and concentrations of a typical batch to minimize the purging time before the desired product could be collected.

For Example 2A, 1.5 kg of Example 1A, 1.34 kg of sodium sulfate, 11.1 L of sodium silicate (3.32 MR, 19.5%) and 20 L of water were added to the recirculation loop, followed by heating to 95° C. with recirculation at 80 L/min with the Silverson operating at 60 Hz (3485 RPM) with the normal rotor/stator configuration. Sodium silicate (3.32 MR, 19.5%) and sulfuric acid (17.1%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected, addition of acid and silicate were stopped and the contents of the loop were allowed to circulate. The silica product in the collection vessel was adjusted to pH 6.0 with the manual addition of sulfuric acid and was then filtered, and washed to a conductivity of ~1500 μS. The pH of the slurry was then readjusted to pH 6.0 with sulfuric acid and spray dried.

For Example 3A, 1.5 kg of Example 1A, 1.34 kg of sodium sulfate, 11.1 L of sodium silicate (2.65 MR, 26.6%) and 20 L of water were added to the recirculation loop, followed by heating to 95° C. with recirculation at 80 L/min with the Silverson operating at 30 Hz (1742 RPM) with the stator screen removed. Sodium silicate (2.65 MR, 26.6%) and sulfuric acid (22.8%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected (500 L), addition of acid and silicate were stopped and the contents of the loop were allowed to circulate.

Then, for surface area reduction, the silica product in the collection vessel was transferred to a batch reactor and heated to 95° C. with stirring at 80 RPM and recirculation at 80 L/min Sodium silicate (2.65 MR, 26.6%) was added to the reactor until a pH of 9.5 (+/−0.2) was reached. Once the pH was reached, sodium silicate (2.65 MR, 26.6%) and sulfuric acid (22.8%) were added at rates of 1.66 L/min and 0.80 L/min, respectively. If needed, the acid rate was adjusted to maintain the pH of 9.5 (+/−0.2). After a total time of 60 minutes, the flow of sodium silicate was stopped and the pH was adjusted to 7.0 with continued addition of sulfuric acid (22.8%) at 0.80 L/min. The batch was digested for 15 minutes at pH 7.0, and then filtered and washed to a conductivity of <1500 µS. Prior to drying, the pH of the silica slurry was adjusted to 5.0 with sulfuric acid and spray dried to a target moisture of 5%.

For Example 4A, 1.5 kg of Example 1A, 1.34 kg of sodium sulfate, 11.1 L of sodium silicate (3.3 MR, 19.5%) and 20 L of water were added to the recirculation loop, followed by heating to 90° C. with recirculation at 60 L/min with the Silverson operating at 30 Hz (1742 RPM) with the stator screen removed. Sodium silicate (3.3 MR, 19.5%) and sulfuric acid (17.1%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected (700 L), addition of acid and silicate were stopped and the contents of the loop were allowed to circulate.

Then, for surface area reduction, the silica product in the collection vessel was transferred to a batch reactor and heated to 95° C. with stirring at 80 RPM. Sodium silicate (3.3 MR, 19.5%) was added to the reactor until a pH of 9.5 (+/−0.2) was reached. Once the pH was reached, sodium silicate (3.32 MR, 19.5%) and sulfuric acid (17.1%) were added at rates of 2.4 L/min and 0.98 L/min, respectively. If needed, the acid rate was adjusted to maintain the pH of 9.5 (+/−0.2). After a total time of 60 minutes, the flow of sodium silicate was stopped and the pH was adjusted to 7.0 with continued addition of sulfuric acid (17.1%) at 0.81 L/min. The batch was digested for 15 minutes at pH 7.0, and then filtered and washed to a conductivity of <1500 µS. Prior to drying, the pH of the silica slurry was adjusted to 5.0 with sulfuric acid and spray dried to a target moisture of 5%.

For Example 5A, 1.5 kg of Example 1A, 1.34 kg of sodium sulfate, 11.1 L of sodium silicate (2.65 MR, 26.6%) and 20 L of water were added to the recirculation loop, followed by heating to 95° C. with recirculation at 80 L/min with the Silverson operating at 30 Hz (1742 RPM) with the stator screen removed. Sodium silicate (2.65 MR, 26.6%) and sulfuric acid (22.8%) were added simultaneously to the loop at a silicate rate of 1.7 L/min and an acid rate sufficient to maintain a pH of 7.5. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected (500 L), addition of acid and silicate were stopped and the contents of the loop were allowed to circulate.

Then, for surface area reduction, the silica product in the collection vessel was transferred to a batch reactor and was heated to 95° C. with stirring at 80 RPM and recirculation at 80 L/min Sodium silicate (2.65 MR, 26.6%) was added to the reactor until a pH of 9.5 (+/−0.2) was reached. Once the pH was reached, sodium silicate (2.65 MR, 26.6%) and sulfuric acid (22.8%) were added at rates of 1.66 L/min and 0.80 L/min, respectively. If needed, the acid rate was adjusted to maintain the pH of 9.5 (+/−0.2). After a total time of 60 minutes, the flow of sodium silicate was stopped and the pH was adjusted to 7.0 with continued addition of sulfuric acid (22.8%) at 0.80 L/min. The batch was digested for 15 minutes at pH 7.0, and then filtered and washed to a conductivity of <1500 µS. Prior to drying, the pH of the silica slurry was adjusted to 5.0 with sulfuric acid and spray dried to a target moisture of 5%.

For Comparative Example 6A, 1.5 kg of Example 1A, 1.34 kg of sodium sulfate, 11.1 L of sodium silicate (3.32 MR, 13.0%) and 20 L of water were added to the recirculation loop, followed by heating to 65° C. with recirculation at 80 L/min with the Silverson operating at 60 Hz (1742 RPM) with the normal rotor/stator configuration. Sodium silicate (3.32 MR, 13.0%) and sulfuric acid (11.4%) were added simultaneously to the loop at a silicate rate of 2.5 L/min and an acid rate sufficient to maintain a pH of 7.4. If necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. The silica product was then collected in a vessel with stirring at 40 RPM while maintaining the temperature at approximately 80° C. After the desired quantity of product was collected (500 L), addition of acid and silicate were stopped and the contents of the loop were allowed to circulate.

Then, for surface area reduction, the silica product in the collection vessel was transferred to a batch reactor and was heated to 95° C. with stirring at 80 RPM and recirculation at 80 L/min Sodium silicate (3.32 MR, 13.0%) was added to the reactor until a pH of 9.5 (+/−0.2) was reached. Once the pH was reached, sodium silicate (3.32 MR, 13.0%) and sulfuric acid (11.4%) were added at rates of 2.30 L/min and 0.83 L/min, respectively. If needed, the acid rate was adjusted to maintain the pH of 9.5 (+/−0.2). After a total time of 175 minutes, the flow of sodium silicate was stopped and the pH was adjusted to 7.0 with continued addition of sulfuric acid (11.4%) at 0.80 L/min. The batch was digested for 10 minutes at pH 7.0, and then filtered and washed to a conductivity of <1500 µS. Prior to drying, the pH of the silica slurry was adjusted to 5.0 with sulfuric acid and spray dried to a target moisture of 5%.

Table I summarizes certain properties of spherical silica particles 3A-5A and comparative silica materials 1A-2A and 6A. As compared to Examples 1A-2A, the silica materials of Examples 3A-5A had excellent stannous compatibility and CPC compatibility, significantly lower BET surface area, CTAB surface area, and pore volume, and higher pour density and pack density. Representative SEM images for Examples 2A-5A are provided as FIGS. 2-5, respectively. Examination of the SEM images demonstrated a narrow particle size distribution and spherical particle morphology for the silica particles of Examples 3A-5A. The respective sphericity factor ($S_{80}$) for each of Examples 3A-5A is greater than 0.9.

Figure 6:
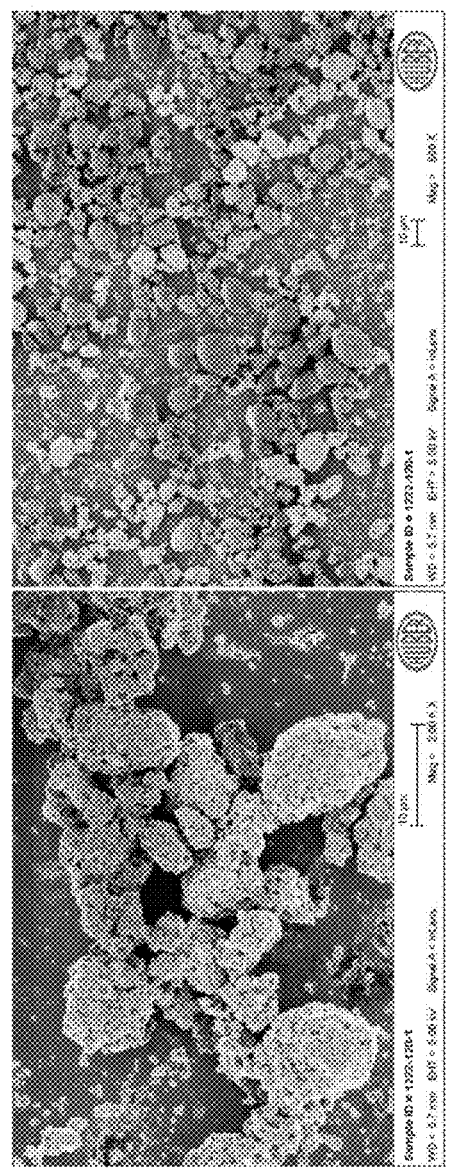
FIG. 6 is Scanning Electron Micrographs of the silica of Example 6A.

SEM images for the comparative silica of Example 6A are provided in FIG. 6. While the silica product of Example 6A was generally spherical (sphericity is less than 0.9), it is not as spherical as the silica materials of Examples 3A-5A. Further, as compared to Example 6A, the larger particle size silica materials of Examples 3A-5A had significantly lower pore volume and higher pour density and pack density (see Table I).

Examples 1B-5B

Example 5C

Toothpaste Formulations and PCR and RDA Testing

Samples of silicas 1A-5A were used in toothpaste formulations 1B-5B at a 20 wt. % loading of the respective silica, and in toothpaste formulation 5C at a 10 wt. % loading of the respective silica, as summarized in Table II. The toothpaste formulations were prepared using standard methods known in the art using the components listed in Table II.

PCR and RDA testing (at the Indiana University School of Dentistry) were conducted on the toothpaste formulations to determine the impact of the silica properties on the PCR and RDA performance. Table III summarizes the PCR and RDA data for the toothpaste formulations. Unexpectedly, as the particle size of the highly spherical particles increased, the PCR and the RDA both decreased. These results are unexpected and contrary to that typically observed with traditional precipitated silica materials (which are irregularly shaped, and not spherical). While not wishing to be bound by theory, it is believed that since RDA testing is performed on an irregular surface comprised of dentin and hollow dentin tubules that are approximately 2-3 µm in size, that the spherical silica particles fall partway into the tubules, and then gouge the opposite wall as they are pushed out of the tubule by the toothbrush as they move across the dentin surface.

Examples 7A-11A

Irregular Silica Particles

Table IV summarizes certain properties of comparative silica materials 7A-11A, which have an irregular and non-spherical particle morphology. Example 7A was a conventional silica material commercially available from Evonik Corporation, and Examples 8A-11A were produced by air milling an unmilled sample of Example 7A to a d50 particle size of 3.5 µm (Example 8A), 6.2 µm (Example 9A), 9.4 µm (Example 10A, broad particle size distribution), and 9.3 µm (Example 11A, narrow particle size distribution).

Examples 7B-11B

Toothpaste Formulations and PCR and RDA Testing

Samples of silicas 7A-11A were used in toothpaste formulations 7B-11B at a 20 wt. % loading of the respective silica, using the same formulations shown in Table II for Examples 1B-5B.

PCR and RDA testing (at the Indiana University School of Dentistry) were conducted on the toothpaste formulations to determine the impact of the silica properties on the PCR and RDA performance. Table V summarizes the PCR and RDA data for the toothpaste formulations. As shown in Table V, as the particle size of the silica increased from 3.5 µm to 9.5 µm, there was no change in either the RDA or the PCR values. Thus, for irregular and non-spherical silica particles, there is no correlation between particle size and RDA and no correlation between particle size and PCR.

Discussion of Examples

By comparing the data in Table III with that of Table V, the behavior of the spherical silica materials is fundamentally (and surprisingly) different from that of traditional dental silicas, which are non-spherical and irregularly shaped. Particle size and particle size distribution can be used to control RDA and PCR with highly spherical materials, whereas for traditional irregularly-shaped silicas, particle size and particle size distribution have no significant effect.

While not wishing to be bound by the following theory, it is believed that the spherical particles initially gouge into the substrate, before they begin rolling across the surface (initially there is a lot of wear, but as the particles begin to roll, the wear is essentially eliminated), whereas a traditional non-spherical and irregularly shaped product would scratch the entire way across the substrate.

Figure 7:
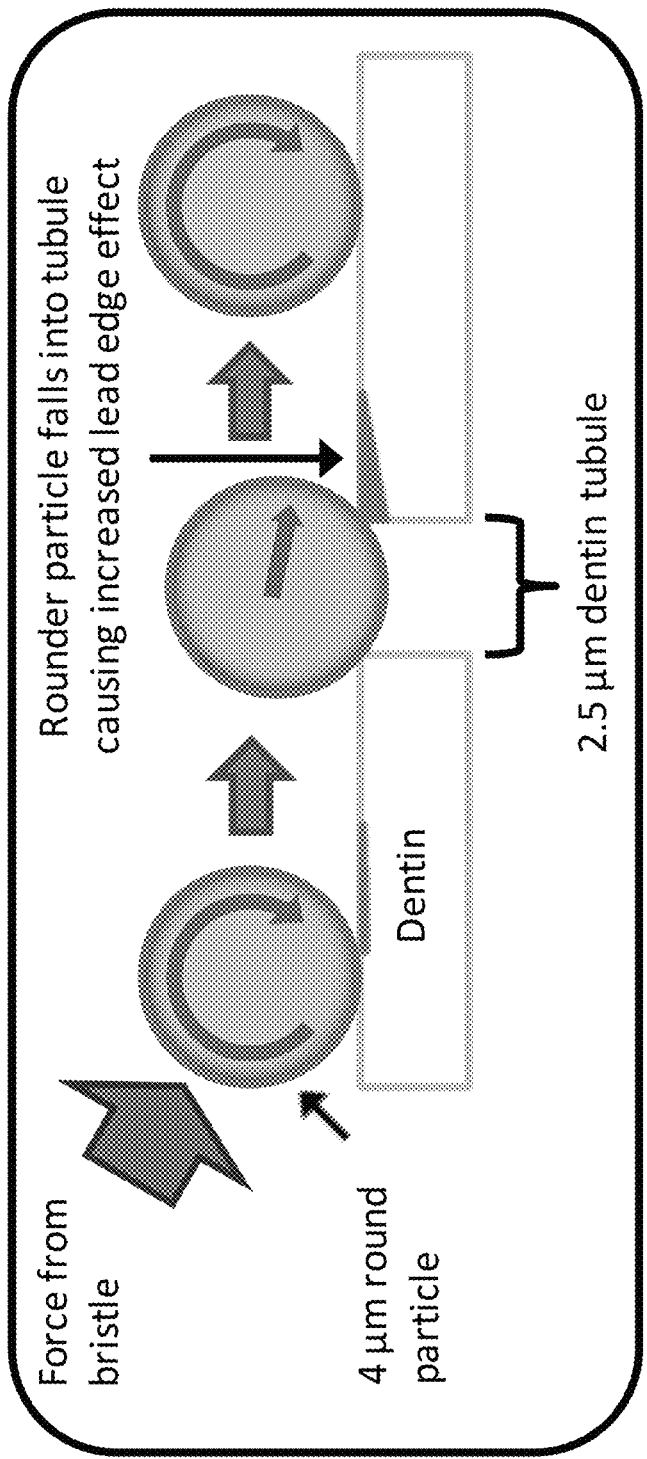
FIG. 7 is a model for a 4 µm spherical particle interacting with a 2.5 µm dentin tubule.

As shown in Table III, the RDA values for spherical products with particle sizes of greater than 8 µm are less than 190. It is postulated that since the dentin surface is essentially non-homogeneous, comprised of both porous mineral and organic content, the spherical particles partially enter tubules and scrape the opposite side as they exit. With very spherical particles, as the particle size is increased, the depth that they can enter a tubule is reduced. This reduction in penetration in the tubule (and increase in particle size) is thought to be the driving factor for reducing RDA. A model for the spherical particle (at a small particle size) interacting with a dentin tubule is illustrated in FIG. 7.

Figure 8:
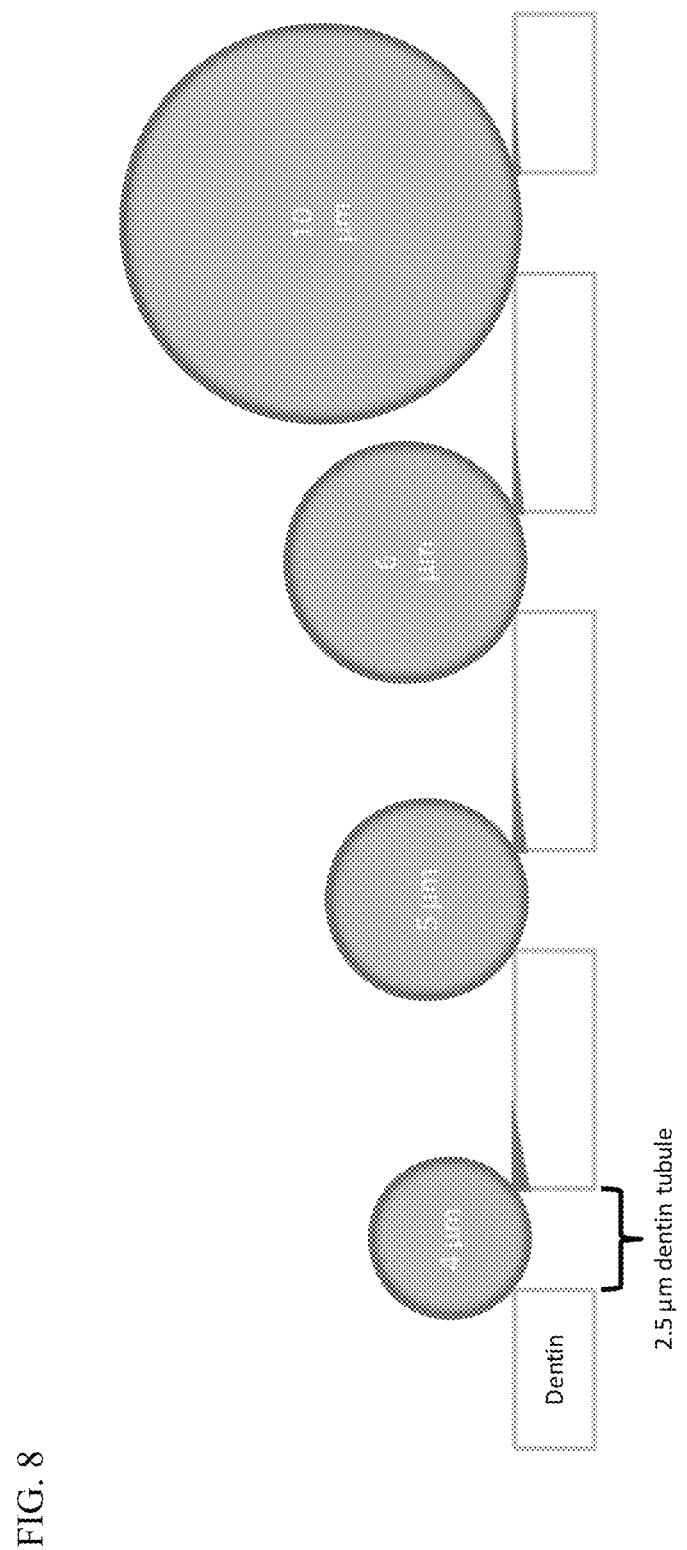
FIG. 8 is a model for spherical particles of increasing particle size (4 µm, 5 µm, 6 µm, 10 µm) interacting with dentin tubules of 2.5 µm.

A simple analogy would be driving over a pothole with a car tire. If the pothole is large relative to the car tire, a large bump is felt as the car passes over the pothole. As the pothole is decreased in size, the intensity of the bump that is felt decreases, until the pothole is small enough that the car tire does not fall very far into the hole. If the pothole was a fixed size, the same effect would be observed as the tires on the car were increased in size. In like manner, a model of spherical particles of increasing particle size (4 µm, 5 µm, 6 µm, 10 µm) interacting with dentin tubules of approximately 2.5 µm in size in shown in FIG. 8. The penetration depth of the particles into the tubules is reduced as particle size increases.

Figure 9:
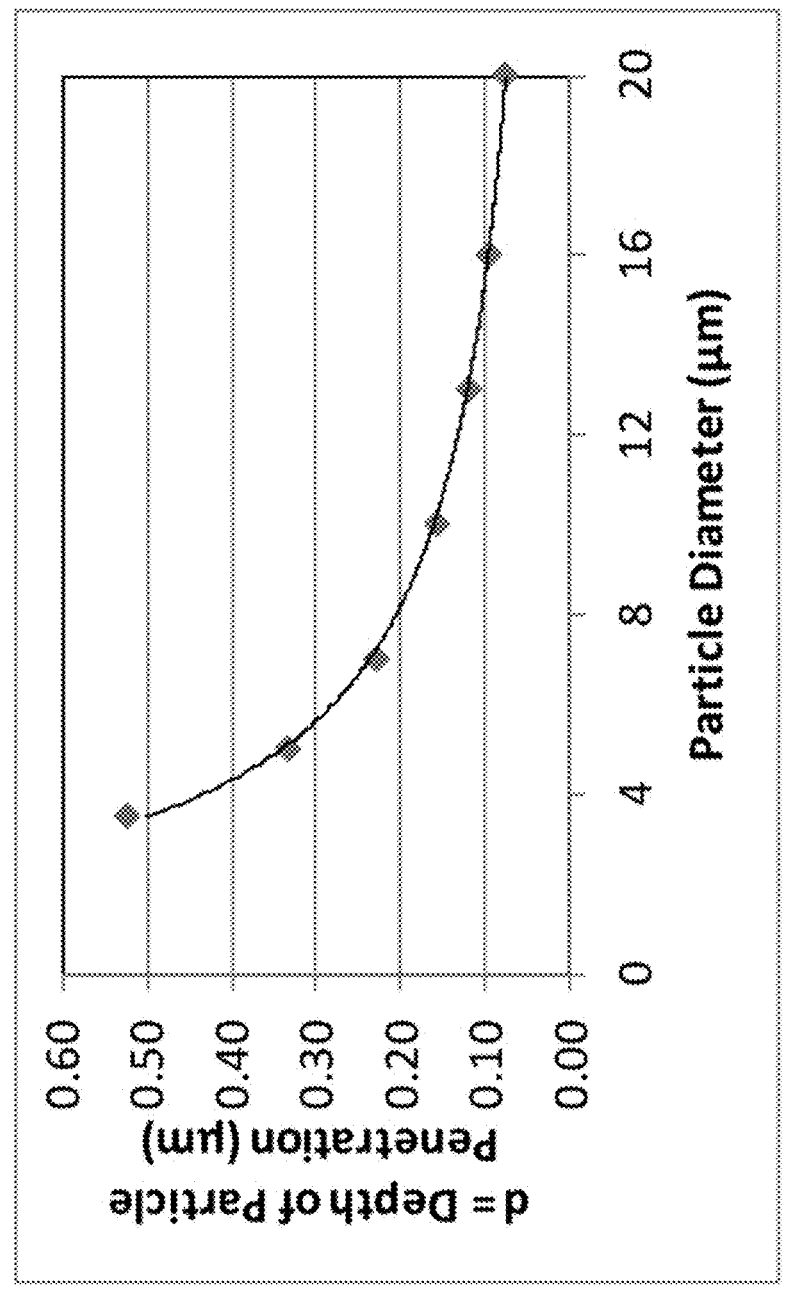
FIG. 9 is a plot of the depth of penetration, in a 2.5 µm width dentin tubule, versus particle diameter for a sphere.

Using geometric calculations, the depth of penetration for a spherical particle can be calculated based upon its diameter, as described by J. M. Fildes et al., Wear 274-275 (2012) 414-422, incorporated herein by reference in its entirety. As it pertains to silica particle sizes and the 2.5 μm width dentin tubules relevant to RDA, a plot of the depth of penetration versus particle diameter for a sphere can be generated (see FIG. 9). There is a reduction in the depth of penetration of highly spherical particles of roughly 80% as the particle size increases from 3.5 μm to 12 μm.

Figure 10:
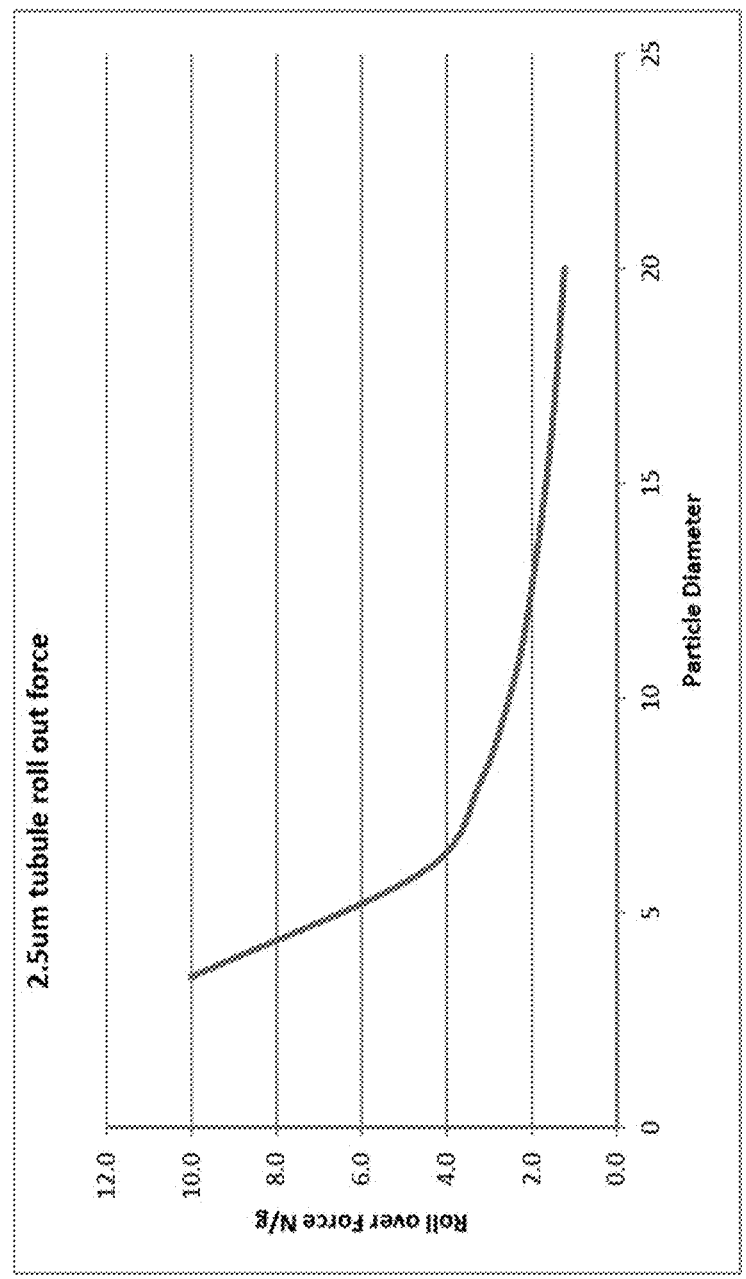
FIG. 10 is a plot of the force required to roll a sphere out of a 2.5 µm width tubule as a function of increasing particle diameter for a sphere.

The force required for a circular wheel (analogous to a spherical particle) to pass over a step of different heights (analogous to a depth of penetration) also can be calculated using formulas in "Physics for Scientists and Engineers" Eighth Edition (2010); Serway|Jewett, incorporated herein by reference in its entirety. Using the assumption that the spherical particle only contacts one part of the tubule as it passes through (with the exception of when it is at the bottom, then the point of contact is a step), a rough estimate of the force required for the particle to exit the tubule can be calculated. Because dentifrice compositions are loaded by weight and numerically there are more small particles than large particles, it is believed that the calculated force in Newtons should be on a weight basis (per gram basis). FIG. 10 graphically represents the decrease in force required for 1 gram of spherical particles to exit a 2.5 μm tubule as a function of increasing particle size. The force is reduced by over 50% as the particle size increases from 6 μm to 12 μm.

In sum, the figures, tables, and discussion above demonstrate that the behavior of the spherical silica materials is fundamentally (and unexpectedly) different from that of traditional dental silicas, which are non-spherical and irregularly shaped, particularly as it pertains to RDA performance. Particle size is a key factor to control RDA and PCR with highly spherical materials, unlike traditional irregularly-shaped silicas, where particle size has no significant effect.

Examples 3D-6D and 12D-13D

Toothpaste Formulations and PCR and RDA Testing

Samples of silicas 3A-6A and 12A-13A were used in tartar-control toothpaste formulations 3D-6D and 12D-13D at a 22 wt. % loading of the respective silica, as summarized in Table VI. The toothpaste formulations were prepared using standard methods known in the art using the components listed in Table VI. Silicas 12A-13A were conventional (irregularly shaped) silicas available from Evonik Corporation, with a nominal d50 particle size in the 8-10 μm range, a BET surface area greater than 20 $m^2$/g, and generally poor stannous compatibility (<50%).

PCR and RDA testing (at the Indiana University School of Dentistry) were conducted on the toothpaste formulations to determine the impact of the silica properties on the PCR and RDA performance. Table VI summarizes the PCR and RDA data for the toothpaste formulations. Toothpaste formulations 3D-5D (containing 22 wt. % of the respective spherical silicas of Examples 3A-5A) had equivalent PCR values to those of Examples 12D-13D; however, the RDA values for the spherical silica formulations were approximately 10% lower than for formulations using irregularly shaped silicas. This benefit is also demonstrated by the higher PCR/RDA ratios for spherical silica Examples 3D-5D.

Toothpaste formulation 6D (containing comparative silica 6A) exhibited a PCR value approximately 10% greater than for Examples 3A-5A, but the RDA value for Example 6D was 260, which would not be acceptable for use due to the RDA value being greater than the upper limit of 250. Example 6D demonstrates that properties of the silica (other than sphericity), as shown in Table I for silica 6A, can lead to unacceptable RDA properties.

TABLE I

| | Examples 1A-6A | | | | | |
|---|---|---|---|---|---|---|
| Example | 1A | 2A | 3A | 4A | 5A | 6A |
| Description | Comparative Silica | Comparative Silica | Spherical Silica | Spherical Silica | Spherical Silica | Comparative Silica |
| Einlehner (mg lost/100 k rev) | 15.2 | 1.4 | 11.5 | 16.3 | 15.3 | 19.5 |
| CPC Compatibility (%) | 0 | 0 | 87 | 81 | 91 | — |
| Stannous Compatibility (%) | 24 | 13 | 89 | 93 | 86 | — |
| BET Surface Area ($m^2$/g) | 56 | 89 | 1 | 2 | 0.5 | 5 |
| Total Hg Intruded Pore Volume (cc/g) | 0.92 | 0.75 | 0.58 | 0.60 | 0.49 | 0.96 |
| CTAB Surface Area ($m^2$/g) | 63 | 56 | 1 | 1 | 1 | 0 |
| Oil Absorption (cc/100 g) | 53 | 66 | 50 | 32 | 38 | 75 |
| Water AbC (cc/100 g) | 70 | 75 | 61 | 66 | 57 | 94 |
| 5% pH | 7.4 | 7.2 | 7.6 | 7.5 | 7.9 | 7.6 |
| Median Particle Size - d50 (μm) | 9.7 | 3.5 | 9.1 | 11.8 | 13.9 | 6.3 |
| Mean Particle Size (μm) | 12.5 | 3.8 | 9.3 | 11.5 | 13.7 | 6.6 |
| d10 (μm) | 2.2 | 2.1 | 1.9 | 1.8 | 2.2 | 1.8 |
| d90 (μm) | 26.8 | 6.0 | 15.7 | 18.8 | 22.1 | 11.1 |
| Ratio of (d90 − d10)/d50 | 2.5 | 1.1 | 1.5 | 1.4 | 1.4 | 1.5 |
| 325 Mesh Residue (wt. %) | 1.12 | 0.01 | 0.26 | 0.20 | 0.03 | 0.09 |
| LOD (wt. %) | 5.0 | 4.3 | 5.8 | 5.3 | 6.1 | 5.0 |
| LOI (wt. %) | 4.1 | 3.8 | 3.2 | 4.5 | 4.0 | 3.8 |
| Sodium Sulfate (%) | 2.08 | 0.82 | 1.85 | 0.35 | 0.35 | — |
| Pour Density (lb/$ft^3$) | 26.0 | 30.2 | 44.6 | 49.9 | 53.8 | 29.2 |
| Pack Density (lb/$ft^3$) | 45.0 | 46.8 | 62.4 | 62.4 | 65.0 | 49.2 |
| Average silica addition rate (%/min) | — | — | 0.44 | 0.42 | 0.44 | 0.44 |

TABLE II

Examples 1B-5B and Example 5C - Toothpaste formulations used for PCR/RDA testing (all values in wt. %)

| Example | 1B | 2B | 3B | 4B | 5B | 5C |
|---|---|---|---|---|---|---|
| Glycerin (99.7%) | 11.000 | 11.000 | 11.000 | 11.000 | 11.000 | 11.000 |
| Sorbitol (70.0%) | 40.007 | 40.007 | 40.007 | 40.007 | 40.007 | 40.007 |
| Deionized water | QS | QS | QS | QS | QS | QS |
| PEG-12 | 3.000 | 3.000 | 3.000 | 3.000 | 3.000 | 3.000 |
| Cekol 2000A | 1.200 | 1.200 | 1.200 | 1.200 | 1.200 | 1.200 |
| Tetrasodium pyrophosphate | 0.500 | 0.500 | 0.500 | 0.500 | 0.500 | 0.500 |
| Sodium saccharin | 0.200 | 0.200 | 0.200 | 0.200 | 0.200 | 0.200 |
| Sodium fluoride | 0.243 | 0.243 | 0.243 | 0.243 | 0.243 | 0.243 |
| Zeodent ® 165 Silica | 1.500 | 1.500 | 1.500 | 1.500 | 1.500 | 5.000 |
| Example 1A | 20 | | | | | |
| Example 2A | | 20 | | | | |
| Example 3A | | | 20 | | | |
| Example 4A | | | | 20 | | |
| Example 5A | | | | | 20 | |
| Example 5A | | | | | | 10 |
| Titanium dioxide | 0.500 | 0.500 | 0.500 | 0.500 | 0.500 | 0.500 |
| Sodium lauryl sulfate | 1.200 | 1.200 | 1.200 | 1.200 | 1.200 | 1.200 |
| Flavor | 0.650 | 0.650 | 0.650 | 0.650 | 0.650 | 0.650 |
| Total | 100 | 100 | 100 | 100 | 100 | 100 |

TABLE III

Examples 1B-5B and Example 5C - PCR and RDA data

| Example | 1B | 2B | 3B | 4B | 5B | 5C |
|---|---|---|---|---|---|---|
| BET Surface Area (m$^2$/g) | 56 | 89 | 1 | 2 | 0.5 | 0.5 |
| Median Particle Size (μm) | 9.7 | 3.5 | 9.1 | 11.8 | 13.9 | 13.9 |
| Mean Particle Size (μm) | 12.5 | 3.8 | 9.3 | 11.5 | 13.7 | 13.7 |
| Example Silica (wt. %) | 20 | 20 | 20 | 20 | 20 | 10 |
| PCR | 106 | 118 | 103 | 96 | 96 | 86 |
| RDA | 180 | 270 | 182 | 169 | 168 | 140 |
| Ratio of PCR/RDA | 0.59 | 0.43 | 0.56 | 0.57 | 0.57 | 0.61 |

TABLE IV

Examples 7A-11A

| | Example | | | | |
|---|---|---|---|---|---|
| | 7A | 8A | 9A | 10A | 11A |
| Einlehner (mg lost/100k rev) | 15.2 | 11.0 | 15.8 | 16.5 | 16.4 |
| BET Surface Area (m$^2$/g) | 56 | 47 | 44 | 45 | 50 |
| CTAB Surface Area (m$^2$/g) | 63 | 40 | 36 | 38 | 26 |
| Oil Absorption (cc/100 g) | 53 | 62 | 50 | 53 | 58 |
| Water AbC (cc/100 g) | 70 | 75 | 68 | 68 | 71 |
| 5% pH | 7.4 | 7.8 | 7.8 | 7.7 | 7.8 |
| LOD (wt. %) | 6.5 | 6.4 | 10.4 | 10.2 | 5.6 |
| Median Particle Size (μm) | 9.7 | 3.5 | 6.2 | 9.4 | 9.3 |
| Mean Particle Size (μm) | 12.5 | 3.8 | 7.6 | 12.5 | 10.1 |
| Ratio of (d90-d10)/d50 | 3.2 | — | — | — | — |
| 325 Mesh Residue (wt. %) | 1.12 | 0.20 | 1.5 | 3.8 | 0.4 |
| Sodium Sulfate (%) | 2.08 | 1.14 | 1.14 | 1.14 | 1.00 |
| Pour Density (lb/ft$^3$) | 26.0 | 17.0 | 22.0 | 26.0 | 26.0 |
| Pack Density (lb/ft$^3$) | 45.0 | 25.0 | 39.0 | 39.0 | 45.0 |

TABLE V

Examples 7B-11B - PCR and RDA data

| | Example | | | | |
|---|---|---|---|---|---|
| | 7B | 8B | 9B | 10B | 11B |
| Median Particle Size (μm) | 9.7 | 3.5 | 6.2 | 9.4 | 9.3 |
| Mean Particle Size (μm) | 12.5 | 3.8 | 7.6 | 12.5 | 10.1 |
| Example Silica (wt. %) | 20 | 20 | 20 | 20 | 20 |
| PCR | 102 | 108 | 103 | 105 | 106 |
| RDA | 212 | 218 | 216 | 222 | 214 |

TABLE VI

Examples 3D-6D and 12D-13D - Toothpaste formulations (all values in wt. %) and PCR and RDA data

| Example | 3D | 4D | 5D | 6D | 12D | 13D |
|---|---|---|---|---|---|---|
| Description | Spherical Silica | Spherical Silica | Spherical Silica | Comparative Silica | Comparative Silica | Comparative Silica |
| Sorbitol solution (70%) | 32.577 | 32.577 | 32.577 | 32.577 | 32.577 | 32.577 |
| Sodium hydroxide (50% soln.) | 1.740 | 1.740 | 1.740 | 1.740 | 1.740 | 1.740 |
| Water | QS | QS | QS | QS | QS | QS |
| Saccharin sodium | 0.450 | 0.450 | 0.450 | 0.450 | 0.450 | 0.450 |

TABLE VI-continued

Examples 3D-6D and 12D-13D - Toothpaste formulations (all values in wt. %) and PCR and RDA data

| Example | 3D | 4D | 5D | 6D | 12D | 13D |
|---|---|---|---|---|---|---|
| Xanthan gum | 0.300 | 0.300 | 0.300 | 0.300 | 0.300 | 0.300 |
| Sodium fluoride | 0.243 | 0.243 | 0.243 | 0.243 | 0.243 | 0.243 |
| Carboxymethylcellulose | 1.050 | 1.050 | 1.050 | 1.050 | 1.050 | 1.050 |
| Sodium acid pyrophosphate | 3.190 | 3.190 | 3.190 | 3.190 | 3.190 | 3.190 |
| Carbomer | 0.300 | 0.300 | 0.300 | 0.300 | 0.300 | 0.300 |
| Flavor | 1.4 | 1.4 | 1.4 | 1.4 | 1.4 | 1.4 |
| Sodium lauryl sulfate (28% soln.) | 6.000 | 6.000 | 6.000 | 6.000 | 6.000 | 6.000 |
| Mica titanium dioxide | 0.400 | 0.400 | 0.400 | 0.400 | 0.400 | 0.400 |
| Silica | | | | | | |
| Example 3A | 22 | | | | | |
| Example 4A | | 22 | | | | |
| Example 5A | | | 22 | | | |
| Example 6A | | | | 22 | | |
| Example 12A | | | | | 22 | |
| Example 13A | | | | | | 22 |
| Total | 100 | 100 | 100 | 100 | 100 | 100 |
| PCR | 101 | 103 | 96 | 114 | 104 | 103 |
| RDA | 202 | 207 | 187 | 260 | 231 | 227 |
| Ratio of PCR/RDA | 0.50 | 0.50 | 0.51 | 0.44 | 0.45 | 0.45 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. Silica particles characterized by:
(i) a d50 median particle size in a range from about 8 to about 20 μm;
(ii) a sphericity factor ($S_{80}$) of greater than or equal to about 0.9;
(iii) a BET surface area in a range from about 0.1 to about 8 m$^2$/g;
(iv) a total mercury intrusion pore volume in a range from about 0.35 to about 1.1 cc/g; and
(v) a loss on ignition (LOI) in a range from about 3 to about 7 wt. %.

Aspect 2. The silica particles defined in aspect 1, wherein the silica particles are further characterized by any suitable BET surface area, or a BET surface area in any range disclosed herein, e.g., from about 0.1 to about 6 m$^2$/g, from about 0.5 to about 5 m$^2$/g, or from about 0.5 to about 2 m$^2$/g.

Aspect 3. The silica particles defined in any one of the preceding aspects, wherein the silica particles are further characterized by any suitable pack density, or a pack density in any range disclosed herein, e.g., from about 40 to about 75 lb/ft$^3$, from about 58 to about 70 lb/ft$^3$, from about 61 to about 72 lb/ft$^3$, or from about 62 to about 65 lb/ft$^3$.

Aspect 4. The silica particles defined in any one of the preceding aspects, wherein the silica particles are further characterized by any suitable pour density, or a pour density in any range disclosed herein, e.g., from about 40 to about 65 lb/ft$^3$, from about 42 to about 60 lb/ft$^3$, from about 43 to about 58 lb/ft$^3$, or from about 44 to about 54 lb/ft$^3$.

Aspect 5. The silica particles defined in any one of the preceding aspects, wherein the silica particles are further characterized by any suitable Einlehner abrasion value, or an Einlehner abrasion value in any range disclosed herein, e.g., from about 7 to about 25, from about 8 to about 20, from about 10 to about 22, or from about 11 to about 17 mg lost/100,000 revolutions.

Aspect 6. The silica particles defined in any one of the preceding aspects, wherein the silica particles are further characterized by any suitable total mercury intrusion pore volume, or a total mercury intrusion pore volume in any range disclosed herein, e.g., from about 0.35 to about 1.1, from about 0.35 to about 0.7, from about 0.35 to about 0.65, from about 0.4 to about 0.65 cc/g, or from about 0.49 to about 0.6 cc/g.

Aspect 7. The silica particles defined in any one of the preceding aspects, wherein the silica particles are further characterized by any suitable Stannous compatibility, or a Stannous compatibility in any range disclosed herein, e.g., from about 40 to about 99%, from about 80 to about 99%, from about 75 to about 95%, from about 80 to about 95%, or from about 86 to about 93%.

Aspect 8. The silica particles defined in any one of the preceding aspects, wherein the silica particles are further characterized by any suitable CPC compatibility, or a CPC compatibility in any range disclosed herein, e.g., from about 70 to about 99%, from about 75 to about 95%, from about 40 to about 95%, from about 78 to about 95%, or from about 81 to about 91%.

Aspect 9. The silica particles defined in any one of the preceding aspects, wherein the silica particles are further characterized by any suitable median particle size (d50) and/or mean particle size (average), or a median particle size (d50) and/or mean particle size (average) in any range disclosed herein, e.g., from about 8 to about 18 μm, from about 9 to about 16 μm, or from about 9 to about 14 μm.

Aspect 10. The silica particles defined in any one of the preceding aspects, wherein the silica particles are further characterized by any suitable ratio of (d90-d10)/d50, or a ratio of (d90-d10)/d50 in any range disclosed herein, e.g., from about 1.1 to about 2.2, from about 1.2 to about 2, or from about 1.3 to about 1.5.

Aspect 11. The silica particles defined in any one of the preceding aspects, wherein the silica particles are further characterized by any suitable water absorption, or a water absorption in any range disclosed herein, e.g., from about 40 to about 75 cc/100 g, from about 42 to about 75 cc/100 g, from about 50 to about 65 cc/100 g, or from about 57 to about 66 cc/100 g.

Aspect 12. The silica particles defined in any one of the preceding aspects, wherein the silica particles are further characterized by any suitable oil absorption, or an oil absorption in any range disclosed herein, e.g., from about 20 to about 75 cc/100 g, from about 25 to about 60 cc/100 g, from about 25 to about 55 cc/100 g, or from about 32 to about 50 cc/100 g.

Aspect 13. The silica particles defined in any one of the preceding aspects, wherein the silica particles are further characterized by any suitable CTAB surface area, or a CTAB surface area in any range disclosed herein, e.g., from 0 to about 10 $m^2/g$, from 0 to about 6 $m^2/g$, from 0 to about 4 $m^2/g$, or from 0 to about 2 $m^2/g$.

Aspect 14. The silica particles defined in any one of the preceding aspects, wherein the silica particles are further characterized by any suitable pH, or a pH in any range disclosed herein, e.g., from about 5.5 to about 9, from about 6.2 to about 8.5, from about 6.8 to about 8.2, or from about 7.5 to about 7.9.

Aspect 15. The silica particles defined in any one of the preceding aspects, wherein the silica particles are further characterized by any suitable 325 mesh residue, or a 325 mesh residue in any range disclosed herein, e.g., less than or equal to about 1.2 wt. %, less than or equal to about 0.6 wt. %, or less than or equal to about 0.3 wt. %.

Aspect 16. The silica particles defined in any one of the preceding aspects, wherein the silica particles are further characterized by any suitable sphericity factor ($S_{80}$), or a sphericity factor ($S_{80}$) in any range disclosed herein, e.g., greater than or equal to about 0.91, greater than or equal to about 0.92, or greater than or equal to about 0.94.

Aspect 17. The silica particles defined in any one of the preceding aspects, wherein the silica particles are further characterized by any suitable RDA at 20 wt. % loading, or a RDA at 20 wt. % loading in any range disclosed herein, e.g., from about 120 to about 200, from about 130 to about 180, or from about 168 to about 182.

Aspect 18. The silica particles defined in any one of the preceding aspects, wherein the silica particles are further characterized by any suitable ratio of PCR/RDA, or a ratio of PCR/RDA in any range disclosed herein, e.g., from about 0.4:1 to about 0.8:1, from about 0.5:1 to about 0.7:1, or from about 0.56:1 to about 0.57:1.

Aspect 19. The silica particles defined in any one of the preceding aspects, wherein the silica particles are further characterized by any suitable loss on drying (LOD), or a LOD in any range disclosed herein, e.g., from about 1 to about 15 wt. %, from about 3 to about 12 wt. %, from about 4 to about 8 wt. %, or from about 5.3 to about 6.1 wt. %.

Aspect 20. The silica particles defined in any one of the preceding aspects, wherein the silica particles are further characterized by any suitable loss on ignition (LOI), or a LOI in any range disclosed herein, e.g., from about 3 to about 6 wt. %, from about 3.2 to about 5.5 wt. %, or from about 3.2 to about 4.5 wt. %.

Aspect 21. The silica particles defined in any one of the preceding aspects, wherein the silica particles are amorphous, or the silica particles are synthetic, or the silica particles are both amorphous and synthetic.

Aspect 22. The silica particles defined in any one of the preceding aspects, wherein the silica particles are precipitated silica particles.

Aspect 23. A process for producing silica particles, the process comprising:
(a) continuously feeding a first mineral acid and a first alkali metal silicate into a loop reaction zone comprising a stream of liquid medium, wherein at least a portion of the first mineral acid and the first alkali metal silicate react to form a base silica product in the liquid medium of the loop reaction zone;
(b) continuously recirculating the liquid medium through the loop reaction zone;
(c) continuously discharging from the loop reaction zone a portion of the liquid medium comprising the base silica product;
(d) adding a second mineral acid and a second alkali metal silicate under surface area reduction conditions to a mixture of water and the base silica product; and
(e) ceasing the addition of the second alkali metal silicate and continuing the addition of the second mineral acid to the mixture to adjust the pH of the mixture to within a range from about 5 to about 8.5 to produce the silica particles.

Aspect 24. The process defined in aspect 23, wherein steps (a)-(c) are performed simultaneously.

Aspect 25. The process defined in aspect 23 or 24, wherein the loop reaction zone comprises a continuous loop of one or more loop reactor pipes.

Aspect 26. The process defined in any one of aspects 23-25, wherein the first mineral acid and the first alkali metal silicate are fed into the loop reaction zone at different points along the loop reaction zone.

Aspect 27. The process defined in any one of aspects 23-26, wherein the portion of the liquid medium discharged from the loop reaction zone is discharged in a volumetric rate proportional to the amount of the first mineral acid and the first alkali metal silicate fed into the loop reaction zone.

Aspect 28. The process defined in any one of aspects 23-27, wherein steps (a)-(c) are performed in a continuous single loop reactor.

Aspect 29. The process defined in any one of aspects 23-28, wherein the liquid medium is recirculated through the loop reaction zone at a rate in a range from about 15 L/min to about 150 L/min, from about 60 L/min to about 100 L/min, or from about 60 L/min to about 80 L/min.

Aspect 30. The process defined in any one of aspects 23-29, wherein the liquid medium is recirculated through the loop reaction zone at a rate ranging from about 50 vol. % per minute (the recirculation rate, per minute, is one-half of the total volume of the liquid medium in the loop reaction zone) to about 1000 vol. % per minute (the recirculation rate, per minute, is ten times the total volume of the liquid medium in the loop reaction zone), or from about 75 vol. % per minute to about 500 vol. % per minute.

Aspect 31. The process defined in any one of aspects 23-30, wherein the liquid medium is recirculated through the loop reaction zone at a pH in a range from about 2.5 to about 10, from about 6 to about 10, from about 6.5 to about 8.5, or from about 7 to about 8.

Aspect 32. The process defined in any one of aspects 23-31, wherein the first mineral acid comprises sulfuric acid, hydrochloric acid, nitric acid, phosphoric acid, or a combination thereof, and the first alkali metal silicate comprises sodium silicate.

Aspect 33. The process defined in any one of aspects 23-32, wherein all (or substantially all, such as greater than 95 wt. %) of the liquid medium is recirculated in step (b).

Aspect 34. The process defined in any one of aspects 23-33, wherein a pump is utilized to recirculate the liquid medium through the loop reaction zone.

Aspect 35. The process defined in any one of aspects 23-34, wherein step (b) is performed at low shear or no shear conditions, e.g., the loop reaction zone does not comprise a stator screen or the loop reaction zone comprises a stator screen with openings greater than 3 $mm^2$ in cross sectional area (or greater than 10 mm$^2$, greater than 50 mm$^2$, greater than 100 mm$^2$, greater than 500 mm$^2$, etc., in cross sectional area), and/or a shear frequency in the loop reaction zone is less than 1,000,000 interactions/min (or less than 750,000 interactions/min, less than 500,000 interactions/min, less than 250,000 interactions/min, etc.).

Aspect 36. The process defined in any one of aspects 23-35, wherein steps (d)-(e) are performed in a vessel separate from the loop reaction zone, such as a stirred batch reactor.

Aspect 37. The process defined in any one of aspects 23-36, wherein the surface area reduction conditions comprises an addition rate of the second alkali metal silicate to the mixture of an average silica addition rate in a range from about 0.2 to about 0.8 wt. % (or from about 0.25 to about 0.7 wt. %, from about 0.3 to about 0.55 wt. %, or from about 0.42 to about 0.44 wt. %) per minute, and/or at a maximum silica addition rate of less than about 1.9 wt. % (or less than about 1.5 wt. %, or less than about 1 wt. %) per minute.

Aspect 38. The process defined in any one of aspects 23-37, wherein the second mineral acid comprises sulfuric acid, hydrochloric acid, nitric acid, phosphoric acid, or a combination thereof, and the second alkali metal silicate comprises sodium silicate.

Aspect 39. The process defined in any one of aspects 23-38, wherein the surface area reduction conditions of step (d) comprise a time period in a range from about 45 minutes to about 5 hours, or from about 1 hour to about 4 hours.

Aspect 40. The process defined in any one of aspects 23-39, wherein the surface area reduction conditions of step (d) comprise a pH in a range from about 9.2 to about 10.2, from about 9.3 to about 10, or from about 9.3 to about 9.7.

Aspect 41. The process defined in any one of aspects 23-40, wherein the surface area reduction conditions of step (d) comprise a temperature in a range from about 90 to about 100° C., or from about 90 to about 95° C.

Aspect 42. The process defined in any one of aspects 23-41, wherein, in step (d), the second alkali metal silicate and the second mineral acid are added to the mixture in any order, e.g., simultaneously, sequentially, alternating, as well as combinations thereof.

Aspect 43. The process defined in any one of aspects 23-42, wherein, in step (e), the addition rate of the second mineral acid to the mixture is at an average rate of addition of no more than 75% greater (no more than 50% greater, or no more than 10% greater) than the average rate of addition of the second mineral acid in step (d).

Aspect 44. The process defined in any one of aspects 23-43, further comprising a step of filtering after step (e) to isolate the silica particles.

Aspect 45. The process defined in any one of aspects 23-44, further comprising a step of washing the silica particles after step (e).

Aspect 46. The process defined in any one of aspects 23-45, further comprising a step of drying (e.g., spray drying) the silica particles after step (e).

Aspect 47. The process defined in any one of aspects 23-46, wherein the silica particles produced are defined in any one of aspects 1-22.

Aspect 48. Silica particles produced by the process defined in any one of aspects 23-46.

Aspect 49. Silica particles defined in any one of aspects 1-22 produced by the process defined in any one of aspects 23-46.

Aspect 50. A composition comprising the silica particles defined in any one of aspects 1-22 or 48-49.

Aspect 51. A dentifrice composition comprising the silica particles defined in any one of aspects 1-22 or 48-49.

Aspect 52. A dentifrice composition comprising from about 0.5 to about 50 wt. % of the silica particles defined in any one of aspects 1-22 or 48-49.

Aspect 53. A dentifrice composition comprising from about 5 to about 35 wt. % of the silica particles defined in any one of aspects 1-22 or 48-49.

Aspect 54. The dentifrice composition defined in any one of aspects 51-53, wherein the composition further comprises at least one of a humectant, a solvent, a binder, a therapeutic agent, a chelating agent, a thickener other than the silica particles, a surfactant, an abrasive other than the silica particles, a sweetening agent, a colorant, a flavoring agent, and a preservative, or any combination thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
   a) binder;
   b) surfactant;
   c) silica particles;
   wherein the silica particles comprise:
   (i) a d50 median particle size in a range from about 6 to about 25 μm;
   (ii) a BET surface area in a range from 0 to about 10 m$^2$/g; and
   (iii) a total mercury intrusion pore volume in a range from about 0.2 to about 1.5 cc/g, and
   wherein the silica particles are further characterized by a stannous compatibility in a range from about 40 to about 99%.

2. The dentifrice composition of claim 1, wherein the d50 median particle size is in a range from about 8 to about 20 μm.

3. The dentifrice composition of claim 1, wherein the silica particles have a sphericity factor (Sso) and the sphericity factor (Sso) is greater than or equal to about 0.9.

4. The dentifrice composition of claim 3, wherein the sphericity factor ($S_{80}$) is greater than or equal to about 0.92.

5. The dentifrice composition of claim 1, wherein the BET surface area is in a range from about 0.05 to about 8 m$^2$/g.

6. The dentifrice composition of claim 5, wherein the BET surface area is in a range from about 0.1 to about 5 m$^2$/g.

7. The dentifrice composition of claim 1, wherein the total mercury intrusion pore volume is in a range from about 0.35 to about 1.1 cc/g.

8. The dentifrice composition of claim 7, wherein the total mercury intrusion pore volume is in a range from about 0.4 to about 0.65 cc/g.

9. The dentifrice composition of claim 1, wherein the silica particles are further characterized by a pack density in a range from about 40 to about 75 lb/ft$^3$.

10. The dentifrice composition of claim 9, wherein the pack density is in a range from about 61 to about 72 lb/ft$^3$.

11. The dentifrice composition of claim 1, wherein the silica particles are further characterized by a pour density in a range from about 40 to about 65 lb/ft$^3$.

12. The dentifrice composition claim 11, wherein the pour density is in a range from about 42 to about 60 lb/ft$^3$.

13. The dentifrice composition of claim 1, wherein the silica particles are further characterized by an Einlehner abrasion value in a range from about 10 to about 25 mg lost/100,000 revolutions.

14. The dentifrice composition of claim 1, wherein the Stannous compatibility is in a range from about 50 to about 99%.

15. The dentifrice composition of claim 1, wherein the silica particles are further characterized by a CPC compatibility in a range from about 55 to about 99%.

16. The dentifrice composition of claim 1, wherein the silica particles are further characterized by a ratio of (d90-d10)/d50 in a range from about 1.1 to about 2.2.

17. The dentifrice composition of claim 16, wherein the ratio of (d90-d10)/d50 is in a range from about 1.2 to about 2.

18. The dentifrice composition of claim 1, wherein the silica particles are further characterized by a water absorption in a range from about 40 to about 75 cc/100 g.

19. The dentifrice composition of claim 18, wherein the water absorption is in a range from about 42 to about 75 cc/100 g.

20. The dentifrice composition of claim 19, wherein the silica particles are further characterized by an oil absorption in a range from about 20 to about 75 cc/100 g.

21. The dentifrice composition of claim 20, wherein the oil absorption is in a range from about 25 to about 55 cc/100 g.

22. The dentifrice composition of claim 1, wherein the silica particles are further characterized by a CTAB surface area in a range from 0 to about 10 m$^2$/g.

23. The dentifrice composition of claim 22, wherein the CTAB surface area is in a range from 0 to about 4 m$^2$/g.

24. The dentifrice composition of claim 1, wherein the silica particles are further characterized by a 325 mesh residue of less than or equal to about 1.2 wt. %.

25. The dentifrice composition of claim 24, wherein the 325 mesh residue is less than or equal to about 0.6 wt. %.

26. The dentifrice composition of claim 1, wherein the silica particles are further characterized by a RDA at 20 wt. % loading of less than about 250.

27. The dentifrice composition of claim 26, wherein the RDA at 20 wt. % loading is in a range from about 80 to about 200.

28. The dentifrice composition of claim 1, wherein the ratio of PCR/RDA, at 20 wt. % loading, is in a range from about 0.4:1 to about 1.1:1.

29. The dentifrice composition of claim 28, wherein the silica particles are further characterized by a ratio of PCR/RDA, at 20 wt. % loading, in a range from about 0.5:1 to about 0.7:1.

30. The dentifrice composition of claim 1, wherein the silica particles are further characterized by a loss on drying (LOD) in a range from about 1 to about 10 wt. %.

31. The dentifrice composition of claim 30, wherein the loss on drying (LOD) is in a range from about 1 to about 5 wt. %.

32. The dentifrice composition of claim 31, wherein the silica particles are further characterized by a loss on ignition (LOI) in a range from about 3 to about 10 wt. %.

33. The dentifrice composition of claim 32, wherein the loss on ignition (LOI) is in a range from about 3 to about 6 wt. %.

34. The dentifrice composition of claim 1, wherein the silica particles are precipitated silica particles.

35. The dentifrice composition of claim 1, wherein the silica particles are amorphous.

36. The dentifrice composition of claim 1, wherein the composition further comprises at least one of a humectant, a solvent, a therapeutic agent, a chelating agent, a thickener other than the silica particles, an abrasive other than the silica particles, a sweetening agent, a colorant, a flavoring agent, and a preservative, or any combination thereof.

* * * * *